United States Patent

Hutchinson et al.

Patent Number: 5,547,950
Date of Patent: Aug. 20, 1996

[54] OXAZOLIDINONE ANTIMICROBIALS CONTAINING SUBSTITUTED DIAZINE MOIETIES

[75] Inventors: Douglas K. Hutchinson; Michael R. Barbachyn, both of Kalamazoo; Steven J. Brickner; Ronald B. Gammill, both of Portage; Mahesh V. Patel, Kalamazoo, all of Mich.

[73] Assignee: The Upjohn Company, Kalamazoo, Mich.

[21] Appl. No.: 332,822

[22] Filed: Oct. 31, 1994

Related U.S. Application Data

[63] Continuation-in-part of PCT/US93/03570, Apr. 21, 1993, which is a continuation-in-part of Ser. No. 880,432, May 8, 1992, abandoned.

[51] Int. Cl.⁶ .................. C07D 413/00; A61K 31/495
[52] U.S. Cl. .................. 514/252; 514/255; 544/369
[58] Field of Search .................. 514/252, 555; 544/369

[56] References Cited

U.S. PATENT DOCUMENTS

| | | | |
|---|---|---|---|
| Re. 29,934 | 3/1979 | Fauran et al. | 544/369 |
| 3,941,789 | 3/1976 | Renth et al. | 260/268 |
| 4,801,600 | 1/1989 | Wang et al. | 514/376 |
| 4,921,869 | 5/1990 | Wang et al. | 514/376 |

FOREIGN PATENT DOCUMENTS

| | | |
|---|---|---|
| 312000 | 4/1989 | European Pat. Off. . |
| 316594 | 5/1989 | European Pat. Off. . |
| 352781 | 1/1990 | European Pat. Off. . |
| WO90/02744 | 3/1990 | WIPO . |

OTHER PUBLICATIONS

Gregory, W. A. et al., "Antibacterials, Synthesis and Structure-Activity Studies of 3-Aryl-2-oxooxazolidines. 1. The B Group," J. Med. Chem. 32:1673-81 (1989).

Gregory, W. A. et al., "Antibacterials. Synthesis and Structure-Activity Studies of 3-Aryl-2-oxooxazolidines. 2. The A Group," J. Med. Chem. 33:2569-78 (1990).

Wang, C-L. J. et al., "Chiral Synthesis of DUP 721, a New Antibacterial Agent," Tetrahedron 45(5):1323-26 (1989).

Park, Chung-Ho et al., "Antibacterials. Synthesis and Structure-Activity Studies of 3-Aryl-2-oxooxazolindines. 4. Multiply-Substituted Aryl Derivatives," J. Med. Chem. 35:1156-65 (1992).

Primary Examiner—Sharon Gibson
Assistant Examiner—Catherine Kilby Scalzo
Attorney, Agent, or Firm—Donald L. Corneglio

[57] ABSTRACT

A compound of structural Formula I:

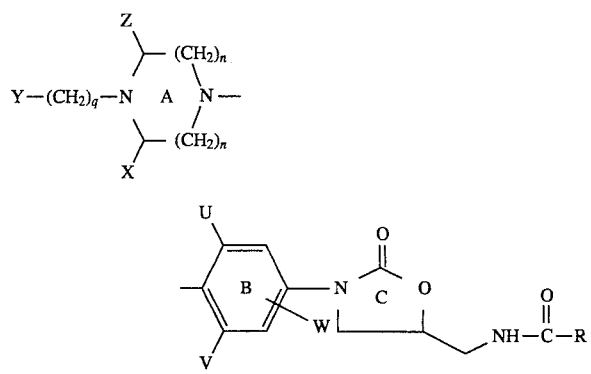

or pharmaceutically acceptable salts thereof wherein: each n is independently 1 to 3; Y is chosen from a–n as defined herein; wherein each occurrence of said $C_{1-6}$ alkyl may be substituted with one or more F, Cl, Br, I, $OR^1$, $CO_2R^1$, CN, $SR^1$, or $R^1$ (where $R^1$ is a hydrogen or $C_{1-4}$ alkyl); X and Z are independently $C_{1-6}$ alkyl, $C_{3-12}$ cycloalkyl or hydrogen, or X and Z form a $C_{0-3}$ bridging group, preferably X and Z are hydrogen; U, V and W are independently $C_{1-6}$ alkyl, F, Cl, Br, hydrogen or a $C_{1-6}$ alkyl substituted with one or more of F, Cl, Br or I, preferably U and V are F and W is hydrogen; R is hydrogen, $C_{1-12}$ alkyl, $C_{3-12}$ cycloalkyl, $C_{1-6}$ alkoxy, $C_{1-6}$ alkyl substituted with one or more F, Cl, Br, I or OH; and q is 0 to 4 inclusive. Oxazolidinone derivatives possessing a substituted diazine moiety bonded to the N-aryl ring are useful antimicrobial agents, effective against a number of human and veterinary pathogens, including multiply-resistant staphylococci and streptococci, as well as anaerobic organisms such as bacteroides and clostridia species, and acid-fast organisms such as *Mycobacterium tuberculosis* and *Mycobacterium avium*.

12 Claims, No Drawings

OXAZOLIDINONE ANTIMICROBIALS CONTAINING SUBSTITUTED DIAZINE MOIETIES

CROSS-REFERENCE TO RELATED APPLICATIONS

This application is a continuation-in-part of PCT/US93/03570, filed Apr. 21, 1993, which was a continuation-in-part of U.S. Ser. No. 07/880,432, filed May 8, 1992, abandoned.

BACKGROUND OF THE INVENTION

The subject invention discloses oxazolidinone derivatives possessing a substituted diazine moiety bonded to an N-aryl ring. The compounds are useful antimicrobial agents, effective against a number of human and veterinary pathogens, including multiply-resistant staphylococci and streptococci, as well as anaerobic organisms such as bacteroides and clostridia species, and acid-fast organisms such as *Mycobacterium tuberculosis* and *Mycobacterium avium*. The compounds are particularly useful because they are effective against the latter organisms which are known to be responsible for infection in persons with AIDS.

INFORMATION DISCLOSURE STATEMENT

PCT/US89/03548 application discloses 5'indolinyl-5β-amidomethyloxazolidinones, 3-(fused-ring substituted)phenyl-5β-amidomethyloxazolidinones, and 3-(nitrogen substituted)-phenyl- 5β-amidomethyloxazolidinones which are useful as antibacterial agents.

Other references disclosing various oxazolidinones include U.S. Pat. Nos. 4,801,600, 4,921,869, Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); and Brittelli, et al., *J. Med. Chem.*, 35, 1156 (1992).

European Patent Publication 352,781 discloses phenyl and pyridyl substituted phenyl oxazolidinones.

European Patent Publication 316,594 discloses 3-substituted styryl oxazolidinones.

European Patent Publication 312,000 discloses phenylmethyl and pyridinylmethyl substituted phenyl oxazolidinones.

SUMMARY OF THE INVENTION

In one aspect the subject invention is a compound of structural Formula I:

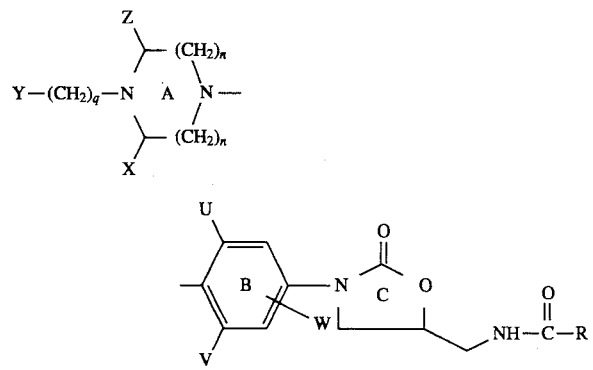

or pharmaceutically acceptable salts thereof wherein:
each n is independently 1 to 3;

Y is a) -hydrogen,
b) —$C_{1-6}$ alkyl, benzyl or -aryl,
c) —OH, —O—$C_{1-6}$ alkyl, —O-vinyl, —O-phenyl, —O—C(O)—$C_{1-6}$ alkyl, —O—C(O)-phenyl (phenyl can be substituted with one to three F, Cl, —$OCH_3$, —OH, $NH_2$ or $C_{1-4}$ alkyl) or —O—C(O)—O—$CH_3$,
d) —S—$C_{1-6}$ alkyl,
e) —$SO_2$—$C_{1-6}$ alkyl, phenylsulfonyl, p-toluenesulfonyl, —$SO_2$—$N(R^3)_2$ (where $R^3$ is independently hydrogen, $C_{1-4}$ alkyl or phenyl which can be substituted with one to three F, Cl, $OCH_3$, OH, $NH_2$, or —$C_{1-4}$ alkyl),
f) —C(O)—$C_{1-6}$ alkyl, benzoyl, 2-benzyloxyethoxycarbonyl, benzyloxycarbonyl, —C(O)—O—$C_{1-6}$ alkyl, —C(O)—$N(R^3)_2$, —C(O)—$CH(R^4)N(R^3)_2$, or —C(O)—$CH(R^4)NH$—C(NH)—$NH_2$ where ($R^4$ is an amino acid side chain),
g) —$N(R^3)_2$, pyridyl, —$N(CH_2)_m$ (where m is 2–6 and forms a cyclic structure with the nitrogen atom and where one or more carbon atoms can be replaced with S, O or $NR^3$), or

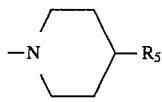

(where $R^5$ is OH, $OCH_3$, $CH_2OH$, $CH_2OCH_3$, $CO_2CH_3$ or $CO_2C_2H_5$),
h) —$C(CH_3)$—N—OR,

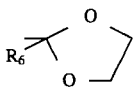   i):

(where $R^6$ is $CH_3$ or hydrogen),

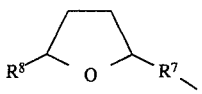   j):

(where $R^7$ is $CH_2$ or C(O) and $R^8$ is —H or =O),

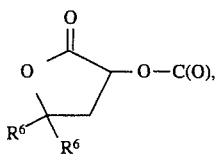   k):

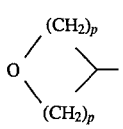

l)

(where p is 1 or 2),

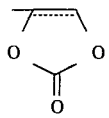   m)

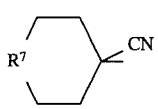   n)

(where $R^7$ is O, S, S(O), $SO_2$, $CH_2$, NH, $NCH_3$, $NC_2H_5$, NCHO, $NCOCH_3$ or $NCO_2CH_3$);
wherein each occurrence of said $C_{1-6}$ alkyl may be substituted with one or more F, Cl, Br, I, $OR^1$, $CO_2R^1$, CN, $SR^1$, or $R^1$ (where $R^1$ is a hydrogen or $C_{1-4}$ alkyl);

X and Z are independently $C_{1-6}$ alkyl, $C_{3-12}$ cycloalkyl or hydrogen, or X and Z form a $C_{0-3}$ bridging group, preferably X and Z are hydrogen;

U, V and W are independently $C_{1-6}$ alkyl, F, Cl, Br, hydrogen or a $C_{1-6}$ alkyl substituted with one or more of F, Cl, Br or I, preferably U and V are F and W is hydrogen;

R is hydrogen, $C_{1-12}$ alkyl, $C_{3-12}$ cycloalkyl, $C_{1-6}$ alkoxy, $C_{1-6}$ alkyl substituted with one or more F, Cl, Br, I or OH; and q is 0 to 4 inclusive.

Preferably, in the above Formula I, U and V are F and W is hydrogen; or U is F and V and W is hydrogen. Preferred forms of Y are selected from the group consisting of H, methyl, ethyl, isopropyl, tert-butyl, benzyl, phenyl, pyridyl, acetyl, difluoroacetyl, hydroxyacetyl, benzoyl, methoxy carbonyl, ethoxy carbonyl, 2-chloroethoxy carbonyl, 2-hydroxyethoxy carbonyl, 2-benzyloxyethoxy carbonyl, 2-methoxyethoxy carbonyl, 2,2,2-trifluoroethoxy carbonyl, cyanomethyl, 2-cyanoethyl, carbomethoxymethyl, 2-carbomethoxyethyl, 2-fluoroethoxy carbonyl, benzyloxy carbonyl, tertary-butoxy carbonyl, methyl sulfonyl, phenyl sulfonyl or paratoluenesulfonyl, more preferred, are methoxy carbonyl or cyanomethyl. Also preferred is where R is methyl, H, methoxy, or $CHCl_2$ and n is one. It is also preferred that the compounds of Formula I are optically pure enantiomers having the S- configuration at C5 of the oxazolidinone ring.

Preferred compounds of the subject invention are (a) 4-(4-(5-((acetylamino)methyl)-2-oxo-3-oxazolidinyl)-2-fluorophenyl)-1-piperazinecarboxylic acid, methyl ester;

(b) 4-(4-(5-((acetylamino)methyl)-2-oxo-3-oxazolidinyl)-2-fluorophenyl)-1-piperazinecarboxylic acid, ethyl ester;

(c) 4-(4-(5-((acetylamino)methyl)-2-oxo-3-oxazolidinyl)phenyl)-1-piperazinecarboxylic acid, methyl ester;

(d) N-((2-oxo-3-(4-(4-(phenylcarbonyl)-1-piperazinyl)phenyl)-5-oxazolidinyl)methyl)acetamide;

(e) N-((3-(4-(3-Fluoro-4-(4-(2-Cyanoethyl)-1-piperazinyl))phenyl)-2-oxo- 5-oxazolidinyl)methyl)-acetamide;

(f) N-((3-(4-(3-Fluoro-4-(4-(2-hydroxyethyl)carbonyl-1-piperazinyl))phenyl)-2-oxo- 5-oxazolidinyl)methyl)-acetamide;

(g) N-((3-(4-(3-Fluoro-4-((phenylcarbonyl)-1-piperazinyl))phenyl)-2-oxo-5-oxazolidinyl)methyl)-acetamide;

(h) 4-[4-[5-[(acetylamino)methyl]-2-oxo-3-oxazolidinyl]-2-fluorophenyl]-1 -piperazinecarboxylic acid, 2-methoxyethyl ester;

(i) 4-[4-[5(acetylamino)methyl]-2-oxo-3-oxazolidinyl]-2-fluorophenyl]-1-piperazineacetonitrile;

(j) (+/−)-N-[[3-[4-[4-(1,4-Dioxopentyl)-1-piperazinyl]-3-fluorophenyl]-2 -oxo-5-oxazolidinyl]methyl)-acetamide;

(k) (S)-N-[[3-[3-fluoro-4-[4-(2-methoxyethyl)-1-piperazinyl]phenyl]-2-oxo- 5-oxazolidinyl]methyl]acetamide; or (l) (S)-N-[[3-[3,5-difluoro-4-[4-(2-methoxyethyl)-1-piperazinyl]phenyl]-2-oxo- 5-oxazolidinyl]methyl]acetamide.

More preferred are compounds (S)-N-[[3-[3-fluoro-4-[4-(hydroxyacetyl)-1-piperazinyl]phenyl]-2-oxo-5-oxazolidinyl]methyl]acetamide (where n=1, q=0, U, X, W and Z are hydrogen, V is fluorine, R is methyl and Y is hydroxyacetyl);

(a) 4-(4-(5-((acetylamino)methyl)- 2-oxo-3-oxazolidinyl)-2-fluorophenyl)-1-piperazinecarboxylic acid, methyl ester; and (i) 4-[4-[5(acetylamino)methyl]-2-oxo-3-oxazolidinyl]-2-fluorophenyl]-1-piperazineacetonitrile.

In another aspect, the subject invention is directed toward a method for treating microbial infections in warm blooded animals by administering to a warm blooded animal in need thereof an effective amount of a compound of Formula I as described above. Preferably, the compound is administered in an amount of from about 0.1 to about 100 mg/kg of body weight/day, more preferably, from about 3.0 to about 50 mg/kg of body weight/day.

DETAILED DESCRIPTION OF THE INVENTION

The present invention discloses diazinyl oxazolidinones of structural Formula I as defined above. The compounds are useful antimicrobial agents, effective against a number of human and veterinary pathogens, including multiply-resistant staphylococci and streptococci, as well as anaerobic organisms such as bacteroides and clostridia species, and acid-fast bacteria such as *Mycobacterium tuberculosis* and *Mycobacterium avium*.

With respect to the above definition, $C_{1-6}$ or $C_{1-12}$ alkyl is methyl, ethyl, propyl, butyl, pentyl, hexyl, etc. and isomeric forms thereof.

Cycloalkyl are three to twelve carbon atoms forming cyclopropyl, cyclobutyl, cyclopentyl, cyclohexyl, etc. and isomeric forms thereof.

Alkoxy are one to six carbons attached to an oxygen forming such groups as methoxy, ethyloxy, butyloxy, etc. and isomeric forms thereof. Further in some instances, groups are described as an alkoxy carbonyl which are named in the compound's nomenclature as an alkyl-ester (such as, methoxy carbonyl and methyl ester).

Aryl is defined as a phenyl, pyridyl or napthyl moiety which can be optionally substituted with one or more F, Cl, Br, I, $OR^1$, $CO_2R^1$, CN, $SR^1$, or $R^1$ (where $R^1$ is a hydrogen or $C_{1-4}$ alkyl).

Pharmaceutically acceptable salts means salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate and the like. These salts may be in hydrated form.

Ring A may be 6–8 atoms in size, and in the larger rings may have either two or three carbons between each nitrogen atom, for example:

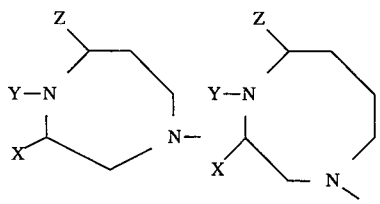

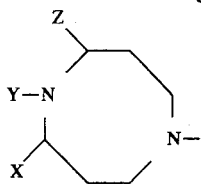

In the larger ring cases, the ring may be bridged to form a bicyclic system as shown in the examples below:

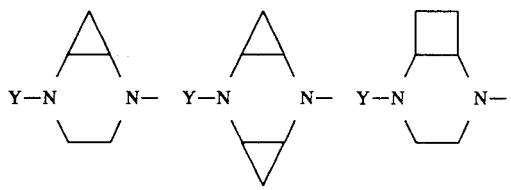

When ring A is 6 atoms in size, then the ring may be optionally substituted at positions X and Z with alkyl groups, cycloalkyl groups, fluoro groups, or bridging alkyl groups, as shown in the following examples below:

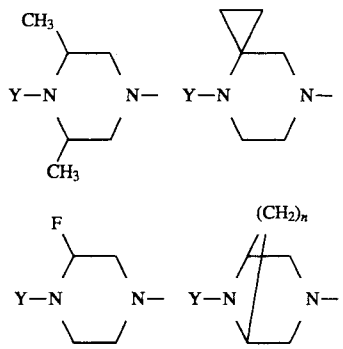

In addition to the above examples, the alternative bicyclic system shown below would also serve as another example:

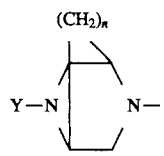

Ring B, in addition to being unsubstituted, can be substituted with one or more halogen atoms in the series fluorine, chlorine or bromine. Thus, the groups U, V, and W on ring B can be independently either hydrogen atoms or halogen atoms in a variety of substitution patterns.

The group Y on the nitrogen atom of ring A can be introduced by standard synthetic methods (described later) from commercially available reagents. Preferably, Y is selected from the group consisting of H, methyl, ethyl, isopropyl, tert-butyl, benzyl, phenyl, pyridyl, acetyl, difluoroacetyl, hydroxyacetyl, benzoyl, methoxy carbonyl, ethoxy carbonyl, 2-chloroethoxy carbonyl, 2-hydroxyethoxy carbonyl, 2-benzoloxyethoxy carbonyl, 2-methoxyethoxy carbonyl, 2,2,2-trifluoroethoxy carbonyl, cyanomethyl, 2-cyanoethyl, carbomethoxymethyl, 2-carbomethoxyethyl, 2-fluoroethoxy carbonyl, benzyloxy carbonyl, tertary-butoxy carbonyl, methyl sulfonyl, phenyl sulfonyl or para-toluenesulfonyl, more preferred, are methoxy carbonyl or cyanomethyl.

The R substituent is preferably methyl, but may be H, methoxy, or $CHCl_2$.

The most preferred compounds of the series would be prepared as the optically pure enantiomers having the (S)-configuration at C5 of the oxazolidinone ring.

Optically pure material could be obtained either by one of a number of asymmetric syntheses or alternatively by resolution from a racemic mixture by selective crystallization of a salt from, for example, intermediate amine 12 (as described in Example 1 and shown in Scheme 1) with an appropriate optically active acid such as dibenzoyl tartrate or 10-camphorsulfonic acid, followed by treatment with base to afford the optically pure amine.

Another route for the preparation of optically pure material would take a different route from those described in the Schemes. Treatment of commercially available 3-fluorophenylisocyanate with commercially available (R)-glycidyl butyrate under the conditions of Herweh and Kauffmann (*Tetrahedron Letters* 1971, 809) would afford the corresponding oxazolidinone in optically pure form with the requisite (S)-configuration at the 5-position of the oxazolidinone ring. Removal of the butyrate group by treatment with potassium carbonate in methanol or sodium methoxide in methanol would give the corresponding alcohol which would be derivatized by standard methods as the mesylate followed by displacement with sodium azide to give the azidomethyl oxazolidinone. Reduction of the azide by hydrogenation followed by acylation of the resultant amine by treatment with acetic anhydride and pyridine would afford the key optically active acetylaminomethyl oxazolidinone. With the acetylaminomethyl oxazolidinone in hand, elaboration of the piperazine moiety would be necessary. Nitration of the fluorooxazolidinone derivative would proceed giving predominantly the nitro group in the position para- to the nitrogen atom of the oxazolidinone ring, and ortho- to the ring fluorine atom. Reduction of the nitro group by hydrogenation would afford the corresponding aniline derivative which upon treatment with bis(2-chloroethyl)amine hydrochloride in the presence of potassium carbonate in refluxing diglyme would afford the optically active piperazine derivative N-((3-(4-(3-fluoro-4-(1-piperazinyl))phenyl-2-oxo-5-oxazolidinyl)methyl)-acetamide (22) which can be used to prepare several of the examples in this disclosure.

These compounds are useful for treatment of microbial infections in humans and other warm blooded animals, under both parenteral and oral administration. Of the Formula I compounds, 4-(4-(5-((acetylamino)methyl)-2-oxo-3-oxazolidinyl)-2-fluorophenyl)-1-piperazinecarboxylic acid, methyl ester (23) and 4-[4-[5(acetylamino)methyl]-2-oxo-3-oxazolidinyl]-2-fluorophenyl]-1-piperazineacetonitrile are most active, and therefore preferred. These are examples of general formula I where ring A is the piperazine moiety.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of Formula I according to this invention are advantageously administered orally in solid and liquid dosage forms.

Antimicrobial activity was tested in vivo using the Murine Assay procedure. Groups of female mice (six mice of 18–20 grams each) were injected intraperitoneally with bacteria which were thawed just prior to use and suspended in brain heart infusion with 4% brewers yeast (*Staphylococcus aureus*) or brain heart infusion (Streptococcus species). Antibiotic treatment at six dose levels per drug was administered one hour and five hours after infection by either oral intubation or subcutaneous routes. Survival was observed daily for six days. $ED_{50}$ values based on mortality ratios were calculated using probit analysis. The subject compounds were compared against well-known antimicrobial as controls. The data are shown in Table 1.

TABLE 1

| In Vivo Activity of Examples 1–5 | | | | |
|---|---|---|---|---|
| Organism | UC # | $ED_{50}$, PO (mg/kg) | | Control, $ED_{50}$, SC (mg/kg) |
| S. aureus | 9213 | Example 1 | 1.8 | Vancomycin 1.8 |
| | | Example 3 | 10.4 | Vancomycin 1.8 |
| | | Example 5 | 10.0 | Vancomycin 4.2 |
| | | Example 6 | 12.0 | Vancomycin 2.5 |
| | | Example 7 | 12.0 | Vancomycin 0.9 |
| | | Example 10 | 9.4 | Vancomycin 1.9 |
| | | Example 36 | 7.9 | Vancomycin 1.7 |
| | | Example 37 | 12.6 | Vancomycin 1.9 |
| S. aureus | 9271 | Example 1 | 4.0 | Vancomycin 5.9 |
| S. aureus | 6685 | Example 1 | 4.0 | Ciprofloxacin 6.6 |
| S. pyogenes | 152 | Example 1 | 2.3 | Clindamycin 2.6 |

In Table 1 the compounds of each of the Examples shown are as follows:

EXAMPLE 1: 4-(4-(5-((Acetylamino)methyl)-2-oxo-3-oxazolidinyl)-2-fluorophenyl)-1-piperazinecarboxylic acid, methyl ester (23);

EXAMPLE 3: 4-(4-(5-((Acetylamino)methyl)-2-oxo-3-oxazolidinyl)phenyl)-1-piperazinecarboxylic acid, methyl ester;

EXAMPLE 5: N-((3-(4-(3-Fluoro-4-(4-(2-Cyanoethyl)-1-piperazinyl))phenyl)-2-oxo-5-oxazolidinyl) methyl)-acetamide;

EXAMPLE 6: 4-(4-(5-((acetylamino)methyl)-2-oxo-3-oxazolidinyl)-2-fluorophenyl)-1-piperazinecarboxylic acid, 2-hydroxyethyl ester;

EXAMPLE 7: N-((3-(4-(3-Fluoro-4-((phenylcarbonyl)-1-piperazinyl))phenyl)-2-oxo-5-oxazolidinyl) methyl)-acetamide;

EXAMPLE 10: (+/−)-N-[[3-[4-[4-(1,4-Dioxopentyl)-1-piperazinyl]-3-fluorophenyl]-2-oxo- 5-oxazolidinyl]methyl)-acetamide;

EXAMPLE 36: (S)-N-[[3-[3-fluoro-4-[4-(2-methoxyethyl)-1-piperazinyl]phenyl]-2-oxo- 5-oxazolidinyl]methyl]acetamide; and EXAMPLE 37: (S)-N-[[3-[3,5-difluoro-4-[4-(2-methoxyethyl)-1-piperazinyl]phenyl]-2-oxo- 5-oxazolidinyl]methyl]acetamide.

The general method for the synthesis of 4-(4-(5-((acetylamino)methyl)-2-oxo-3-oxazolidinyl)- 2-fluorophenyl)-1-piperazinecarboxylic acid, methyl ester (23) and 4-(4-(5-((acetylamino)methyl)- 2-oxo-3-oxazolidinyl)-2-fluorophenyl)-1-piperazinecarboxylic acid, ethyl ester (24) is described in Example 1 and 2, respectively, as well as being structurally represented in Schemes 1 and 2, below. (The compounds used are identified by chemical name followed by a numeral designation from the Schemes for simplicity.) Commercially available difluoronitrobenzene (2) is treated with excess piperazine to afford displacement product 3. After protection as the tert-butoxy carbonyl (BOC) derivative affording 4, reduction of the nitro group with the ammonium formate-Pd/C reagent system afforded aniline derivative 5. Protection of 5 afforded benzyloxy carbonyl (CBZ) derivative 6 which was allylated as shown to produce 7. Osmylation of 7 using the method of Kelly and VanRheenen, *Tetrahedron Letters,* 1973 (1976), gave diol 8 which cyclized upon treatment with potassium carbonate in refluxing acetonitrile to afford oxazolidinone 9. Mesylation of 9 under classical conditions afforded mesylate 10 which undergoes smooth displacement with sodium azide to form azide 11. Reduction of azide 11 by hydrogenation over Pd/C gave amine 12 which was acylated in situ with acetic anhydride and pyridine to afforded BOC-protected oxazolidinone intermediate 4-(4-( 5-((acetylamino)methyl)-2-oxo-3-oxazolidinyl)-2-fluorophenyl)-1-piperazinecarboxylic acid, 1,1-dimethylethyl ester (21).

Deprotection with trifluoroacetic acid afforded the key intermediate for analog preparation, N-((3-(4-(3-fluoro-4-(1-piperazinyl))phenyl)-2-oxo-5-oxazolidinyl)methyl)-acetamide (22). Treatment of (22) with either methyl chloroformate or ethyl chloroformate under preferably Schotten-Baumann conditions (NaHCO₃/acetone-water) afforded 4-(4-(5-((acetylamino)methyl)- 2-oxo-3-oxazolidinyl)-2-fluorophenyl)-1-piperazinecarboxylic acid, methyl ester (23) and 4-(4-(5-((acetylamino)methyl)-2-oxo-3-oxazolidinyl)-2-fluorophenyl)- 1-piperazinecarboxylic acid, ethyl ester (24), respectively.

Although the route explained above and described in Example 1 can be used to prepare all of the subject compounds, a less efficient route may be used to prepare intermediates leading to other of the subject compounds such as N-((2-oxo-3-(4-(4-((phenylcarbonyl)-1-piperazinyl)phenyl)- 5-oxazolidinyl)methyl acetamide (20) and 4-(4-(5((acetylamino)methyl)-2-oxo- 3-oxazolidinyl)phenyl)-1-piperazinecarboxylic acid, methyl ester (19). For instance, diol 13, prepared from piperazine and p-fluoronitrobenzene in a manner identical to that described for diol 8 in Scheme I, is treated with one equivalent of either mesyl chloride or tosyl chloride to afford the mono-derivatized material 14, along with unchanged starting material and bis-derivatized material. After chromatographic isolation of mesylate 14a or tosylate 14b, treatment of either material with sodium azide afforded the azido alcohol 15. Treatment of 15 with base effected cyclization to afford the oxazolidinone 16, which in turn can be converted to acetamide derivative 17 by the one-pot reduction-acylation procedure described in Example 1. As shown, solvolytic deprotection of 17 afforded N-((2-oxo-3-(4-(1-piperazinyl)phenyl)- 5-oxazolidinyl)methyl)-acetamide (18), which can then be acylated to form the two non-fluorinated analogs, 4-(4-(5-((acetylamino)methyl)-2-oxo-3-oxazolidinyl)phenyl)-1-piperazinecarboxylic acid, methyl ester (19) and N-((2-oxo-3-(4-(4-(phenylcarbonyl)-1-piperazinyl)phenyl)-5-oxazolidinyl)methyl)-acetamide (20).

Preparation of analogs of 4-(4-(5-((acetylamino)methyl)-2-oxo-3-oxazolidinyl)-2-fluorophenyl)- 1-piperazinecarboxylic acid, methyl ester (23) and 4-(4-(5-((acetylamino)methyl)- 2-oxo-3-oxazolidinyl)-2-fluorophenyl)-1-piperazinecarboxylic acid, ethyl ester (24) can be envisioned simply by substitution of other cyclic amines for piperazine, other nitrobenzene derivatives for 2, or by treatment of N-((3-(4-(3-fluoro-4-(1-piperazinyl))phenyl)- 2-oxo-5-oxazolidinyl)methyl)-acetamide (22) (or its analogs) with other acylating or alkylating agents.

EXAMPLE 1

4-(4-(5-((Acetylamino)methyl)-2-oxo-3-oxazolidinyl)-2-fluorophenyl)-1-piperazinecarboxylic acid, methyl ester (23)

(a) Preparation of 1-(2-Fluoro-4-nitrophenyl)piperazine (3):

A solution of 12.0 g (75.42 mmol) of 3,4-difluoronitrobenzene (2) in 150 mL of acetonitrile was treated with 16.24 g (188.6 mmol) of piperazine, followed by warming at reflux for 3 hours. The solution was cooled to ambient temperature and was concentrated in vacuo. The residue was diluted with 200 mL of water and was extracted with ethyl acetate (3×250 mL). The combined organic layers were extracted with water (200 mL) and saturated NaCl solution (200 mL), followed by drying (Na₂SO₄). The solution was concentrated in vacuo to afford an orange oil which was chromatographed over 450 g of 230–400 mesh silica gel eluting initially with dichloromethane until the least polar fractions had eluted and then elution was continued with 2% (v/v) methanol-chloroform and then with 10% (v/v) methanol-chloroform. These procedures afforded 13.83 g (81%) of the desired piperazine derivative 3, mp=68.5°–71° C.

(b) Preparation of 1-(tert-Butoxycarbonyl)-4-(2-fluoro-4-nitrophenyl)piperazine (4):

A solution of 12.0 g (53.29 mmol) of nitro derivative 3 in 110 mL tetrahydrofuran was treated dropwise with a solution of 14.53 g (66.61 mmol) of di-tert-butyldicarbonate in 110 mL of tetrahydrofuran. After addition, the solution was stirred at ambient temperature for 24 hours. The solution was concentrated in vacuo and the residue was chromatographed over 450 g of 230–400 mesh silica gel during with 20% (v/v) ethyl acetate in hexane, 30% (v/v) ethyl acetate in hexane and finally with 50% (v/v) ethyl acetate in hexane. These procedures afforded 16.6 g (96%) of BOC derivative 4 as a yellow solid, mp=151°–153.5° C.

(c) Preparation of 1-(tert-Butoxycarbonyl)-4-(2-fluoro-4-aminophenyl)piperazine (5):

A solution of 1.73 g (5.32 mmol) of nitro compound 4 in 30 mL methanol and 20 mL tetrahydrofuran and 10 mL ethyl acetate was treated with 1.68 g (26.59 mmol) of ammonium formate and 200 mg of 10% palladium on carbon. Gas evolution became immediately apparent, and subsided after ca. 30 minutes. The mixture was stirred overnight and was then filtered through celite, washing the filter cake with methanol. The filtrate was concentrated in vacuo, dissolved in 50 mL ethyl acetate and extracted with water (2×30 mL) and saturated NaCl solution (30 mL). Drying (Na₂SO₄) and concentration in vacuo afforded 1.6 g (ca. 100%) of amine 5 as a brown solid, sufficiently pure for use in the next step.

(d) Preparation of 1-(tert-Butoxycarbonyl)-4-(2-fluoro-4-benzyloxycarbonylamino)piperazine (6):

A solution of 1.57 g (5.32 mmol) of amine 5 and 806 mg (0.84 mL, 6.65 mmol) of dimethylaniline in 25 mL of tetrahydrofuran at –20° C. was treated dropwise with 1.0 g (0.84 mL, 5.85 mmol) of benzyl chloroformate. The solution was stirred at –20° C. for 30 minutes, followed by warming to ambient temperature. The mixture was diluted with 125 mL ethyl acetate and was extracted with water (2×50 mL) and saturated NaCl solution (50 mL). Drying (Na₂SO₄) and concentration in vacuo afforded and inhomogeneous material which was adsorbed on silica gel and chromatographed over 115 g of 230–400 mesh silica gel, eluting with 18% (v/v) ethyl acetate in hexane and then with 25% (v/v) ethyl acetate in hexane, and finally with 30% (v/v) ethyl acetate in hexane. These procedures afforded 1.15 g (50%) of the CBZ derivative 6 as a white solid, mp=150°–153° C.

(e) Preparation of 1-(tert-Butoxycarbonyl)-4-(2-fluoro-4-benzyloxycarbonylallylamino) piperazine (7):

A solution of 1.15 g (2.68 mmol) of the CBZ derivative 6 in 10.2 mL dimethylformamide was treated portionwise with 77 mg (129 mg of 60% in oil, 3.21 mmol) of sodium hydride followed by stirring at ambient temperature for 20 minutes. The solution was treated with 356 mg (0.26 mL, 2.95 mmol) of allyl bromide followed by stirring at ambient temperature for 18 hours. The solution was cautiously treated with 75 mL water and was extracted with diethyl ether (3×100 mL). The combined organic layers were extracted with saturated sodium chloride solution (100 mL) and dried ($Na_2SO_4$). Concentration in vacuo afforded an inhomogeneous material which was dissolved in dichloromethane and dried ($Na_2SO_4$). Concentration in vacuo afforded an amber oil which was chromatographed over 60 g 230–400 mesh silica gel eluting with 25% (v/v) ethyl acetate in hexane. These procedures afforded 1.12 g (90%) of the allyl derivative 7 as an oil.

(f) Preparation of 1-(tert-butoxycarbonyl)-4-[2-fluoro-4-benzyloxycarbonyl(2,3-dihydroxyprop- 1-yl)aminophenyl]piperazine (8):

A solution of 2.18 g (4.64 mmol) of allyl compound 7 and 3.26 g (27.86 mmol) of N-methylmorpholine N-oxide in 21 mL acetone and 6.4 mL water was treated with 5 mL of a 2.5% (w/v) solution of osmium tetroxide in tert-butyl alcohol. The resulting solution was stirred at ambient temperature for 24 hours. The solution was cooled to 0° C. and 25 mL of saturated $NaHSO_3$ solution was added, followed by stirring at 0° C. for 15 minutes and then warming to ambient temperature for 2 hours. The mixture was diluted with 50 mL water and 50 mL saturated NaCl solution, followed by extraction with ethyl acetate (5×100 mL). The combined organic layers were dried ($Na_2SO_4$) and concentrated in vacuo to afford a brown oil. This material was chromatographed over 150 g of 230–400 mesh silica gel, eluting with 10% (v/v) methanol in chloroform. These procedures afforded 2.0 g (86%) of the diol 8 as an off-white hygroscopic rigid foam.

(g) Preparation of 3-[3-fluoro-4-(4-tert-butoxycarbonylpiperazin-1-yl)phenyl]-5-hydroxymethyl- 2-oxazolidinone (9):

A solution of 2.0 g (4.01 mmol) of diol 8 in 20 mL acetonitrile was treated with 1.1 g (8.02 mmol) of potassium carbonate followed by warming at reflux for 3 hours. The solution was cooled and concentrated in vacuo. The residue was dissolved in 100 mL ethyl acetate and the resulting solution was extracted with water (2×50 mL) and with saturated NaCl solution (50 mL). Drying ($Na_2SO_4$) and concentration in vacuo afforded an oil which was chromatographed over 80 g of 230–400 mesh silica gel eluting with 20% (v/v) acetone in dichloromethane. These procedures afforded 1.6 g (100%) of oxazolidinone 9 as a white solid, mp=144°–146.5° C.

(h) Preparation of 3-[3-Fluoro-4-(4-tert-butoxycarbonylpiperazin-1-yl)phenyl]- 5-methanesulfonyloxymethyl-2-oxazolidinone (10):

A solution of 375 mg (0.95 mmol) of oxazolidinone 9 and 144 mg (0.20 mL, 1.42 mmol) triethylamine in 3.8 mL dichloromethane at 0° C. was treated dropwise with 130 mg (0.09 mL, 1.14 mmol) of methanesulfonyl chloride followed by stirring at 0° C. for 1 hour. The solution was diluted with 30 mL dichloromethane and was extracted with water (2×25 mL) and with saturated $NaHCO_3$ (25 mL). Drying ($Na_2SO_4$) and concentration in vacuo afforded 440 mg (98%) of mesylate 10 as a white solid, sufficiently pure for use in the next step.

(i) Preparation of 3-[3-Fluoro-4-(4-tert-butoxycarbonylpiperazin-1-yl)phenyl]-5-azidomethyl- 2-oxazolidinone (11):

A solution of 440 mg (0.93 mmol) of mesylate 10 in 22 mL acetone was treated with a solution of 604 mg (9.29 mmol) of sodium azide in 6.4 mL water. The mixture was warmed at reflux for 18 hours. The mixture was cooled and a solution of 600 mg of sodium azide in 6 mL water was added followed by warming at reflux for an additional 18 hours. The mixture was cooled and a solution of 1.2 g of sodium azide in 12 mL water was added followed by warming at reflux for 24 hours. The mixture was cooled and diluted with 60 mL water and extracted with ethyl acetate (3×75). The combined organic layers were extracted with 100 mL saturated NaCl solution followed by drying ($Na_2SO_4$). Concentration in vacuo afforded 358 mg (92%) of azide 11 as a white solid, mp=130.5° C.–132.5° C., sufficiently pure for use in the next step.

(j) Preparation of 3-(3-Fluoro-4-(4-tert-butoxycarbonylpiperazin-1-yl)phenyl)-5-aminomethyl- 2-oxazolidinone (12) and 3-[3-fluoro-4-tert-butoxycarbonylpiperazin-1-yl)phenyl]-5-acetylaminomethyl-2-oxazolidinone (21):

A solution of 1.42 g (3.38 mmol) of the azide 11 in 200 mL ethyl acetate was treated with 400 mg of 10% Palladium on carbon followed by hydrogenation at atmospheric pressure for 48 hours. The resulting ethyl acetate solution of 12 was treated with 1.34 g (1.37 mL, 16.9 mmol) of pyridine and 870 mg (0.80 mL, 8.5 mmol) of acetic anhydride followed by stirring at ambient temperature for 48 hours. The solution was treated with 1.37 mL pyridine and 0.8 mL acetic anhydride followed by stirring at ambient temperature for another 48 hours. The solution was filtered through celite, washing the filter cake with ethyl acetate. The filtrate was washed with water (4×50 mL), 1.0M $CuSO_4$ solution (50 mL), and again with water (50 mL). Drying ($Na_2SO_4$) and concentration in vacuo afforded a foam which was diluted with dichloromethane and stirred for 1 hour with saturated $NaHCO_3$ solution. The mixture was extracted with dichloromethane and the combined organic layers were dried ($Na_2SO_4$) and concentrated in vacuo to afford an amber oil which was chromatographed over 74 g of 230–400 mesh silica gel, eluting with 2% (v/v) methanol in dichloromethane and then with 5% (v/v) methanol in dichloromethane. These procedures afforded 1.19 g (81%) of 3-(3-fluoro-4-tert-butoxycarbonylpiperazin- 1-yl)phenyl)-5-acetylaminomethyl-2-oxazolidinone (21) as a rigid off-white foam, mp=162°–164° C.

(k) Preparation of N-((3-(4-(3-fluoro-4-(1-piperazinyl))phenyl)-2-oxo- 5-oxazolidinyl)methyl)-acetamide (22):

A solution of 1.19 g (2.73 mmol) of BOC derivative 3-(3-fluoro-4-tert-butoxycarbonylpiperazin- 1-yl)phenyl)-5-acetylaminomethyl-2-oxazolidinone (21) in 40 mL dichloromethane at 0° C. was treated with 15 mL trifluoroacetic acid. The solution was stirred at 0° C. for 30 minutes followed by warming to ambient temperature, at which point the reaction was complete. The solution was concentrated in vacuo and the residue was diluted with ethyl acetate and saturated $NaHCO_3$ solution. The aqueous layer was extracted with ethyl acetate, and it became evident that a large part of the product remained in the aqueous layer. The aqueous layer was adjusted to pH 14 by addition of 50% NaOH solution. Extraction with ethyl acetate followed by drying ($Na_2SO_4$) and concentration in vacuo afforded 179 mg of an amber oil. This material was subjected to radial chromatography on a 2 mm plate eluting with 10% (v/v) methanol in chloroform and then with 15% (v/v) methanol in chloroform. These procedures afforded 125 mg (79%) of N-((3-(4-(3-fluoro-4-(1-piperazinyl))phenyl)- 2-oxo-5-oxazolidinyl)methyl)-acetamide (22) as an off-white rigid foam.

(l) Preparation of 4-(4-(5-((Acetylamino)methyl)-2-oxo-3-oxazolidinyl)- 2-fluorophenyl)-1-piperazinecarboxylic acid, methyl ester (23):

A solution of 120 mg (0.36 mmol) of N-((3-(4-(3-fluoro-4-(1-piperazinyl))phenyl)- 2-oxo-5-oxazolidinyl)methyl)-acetamide and 60 mg (0.71 mmol) of solid NaHCO$_3$ in 1.5 mL acetone and 0.7 mL water at 0° C. was treated with 37 mg (30 μL, 0.39 mmol) of methyl chloroformate. The solution was stirred at 0° C. for 1 hour, followed by dilution with 20 mL water. The mixture was extracted with 30 mL ethyl acetate and the organic layer was then extracted with water (2×10 mL) and saturated NaHCO$_3$ (10 mL). The solution was then dried (Na$_2$SO$_4$) and concentrated in vacuo to afford 95 mg of crude product. This material was subjected to radial chromatography using a 2 mm plate eluting with 33% (v/v) acetone in dichloromethane and then with 50% (v/v) acetone in dichloromethane. These procedures afforded 81 mg (57%) of 4-(4-(5-((acetylamino)methyl)-2-oxo-3-oxazolidinyl)- 2-fluorophenyl)-1-piperazinecarboxylic acid, methyl ester (23) as a white solid, mp=177°–179° C.

EXAMPLE 2

4-(4-(5-((Acetylamino)methyl)-2-oxo-3-oxazolidinyl)-2-fluorophenyl)-1-piperazinecarboxylic acid, ethyl ester (24)

The same procedure as followed in Example 1, steps a–k, were followed. Then a solution of 100 mg (0.30 mmol) of N-((3-(4-(3-fluoro-4-(1-piperazinyl))phenyl)- 2-oxo-5-oxazolidinyl)methyl)-acetamide (23) (the product from step k above) and 50 mg (0.59 mmol) of solid NaHCO$_3$ in 2 mL acetone and 1 mL water at 0° C. was treated with 35 mg (31 μL, 0.33 mmol) of ethyl chloroformate. The solution was stirred at 0° C. for 2 hours, followed by warming to ambient temperature for 18 hours. The solution was diluted with 30 mL water and was extracted with 40 mL ethyl acetate. The organic layer was washed with 30 mL water and 30 mL saturated NaHCO$_3$ solution. Drying (Na$_2$SO$_4$) and concentration in vacuo afforded a white solid. This material was subjected to radial chromatography on a 2 mm plate, eluting with 2% (v/v) methanol in chloroform. These procedures afforded 70 mg (58%) of 4-(4-( 5-((acetylamino)methyl)-2-oxo-3-oxazolidinyl)-2-fluorophenyl)-1-piperazinecarboxylic acid, ethyl ester (24) as a white solid, mp=224°–226° C.

EXAMPLE 3

4-(4-(5-((Acetylamino)methyl)-2-oxo-3-oxazolidinyl)-phenyl)-1-piperazinecarboxylic acid, methyl ester Following the procedure of Example 1 the subject compound was prepared by substituting 4-fluoronitrobenzene for the starting material 3,4-difluoronitrobenzene (2).

EXAMPLE 4

N-((2-Oxo-3-(4-(4-(benzoyl)-1-piperazinyl)phenyl)-5-oxazolidinyl)methyl)-acetamide Following the procedure of Example 2 the subject compound was prepared by substituting 4-fluoronitrobenzene for the starting material 3,4-difluoronitrobenzene (2).

EXAMPLE 5

N-((3-(4-(3-Fluoro-4-(4-(2-Cyanoethyl)-1-piperazinyl))phenyl)-2-oxo-5-oxazolindinyl)methyl)-acetamide A solution of 75 mg (0.22 mmol) of N-((3-(4-(3-fluoro-4-(1-piperazinyl))phenyl)-2-oxo-5-oxazolidinyl)methyl)-acetamide (22) (Ex. 1, Part k.) in 5 mL methanol was treated with 13 mg (17 μL, 0.25 mmol) of acrylonitrile followed by warming at reflux for 3 hours. The solution was cooled and concentrated in vacuo. The residue was subjected to radial chromatography on a 4 mm plate eluting with 5% (v/v) methanol in chloroform. These procedures afforded 84 mg (97%) of the desired nitrile, N-((3-(4-(3-Fluoro-4-(4-(2-Cyanoethyl)- 1-piperazinyl))phenyl)-2-oxo-5-oxazolidinyl)methyl)-acetamide, as a white solid, mp=125°–130° C.

EXAMPLE 6

4-(4-(5-((acetylamino)methyl)-2-oxo-3-oxazolidinyl)-2-fluorophenyl)-1-piperazinecarboxylic acid, 2-hydroxyethyl ester A solution of 208 mg (0.25 mmol) of N-((3-(4-(3-fluoro-4-(1-piperazinyl))phenyl)-2-oxo- 5-oxazolidinyl)methyl)-acetamide (22) (Ex. 1, Part k.) in 3 mL acetone and 2 mL water was treated with 21 mg (0.25 mmol) of sodium bicarbonate followed by cooling to 0° C. The mixture was treated with a solution of 54 mg (0.25 mmol) of 2-benzyloxyethyl chloroformate in 2 mL of acetone. The solution was allowed to warm to ambient temperature over 22 hours, followed by dilution with 30 mL ethyl acetate and extraction with water (3×30 mL) and saturated sodium bicarbonate solution (20 mL). The solution was dried (Na$_2$SO$_4$) and concentrated in vacuo to afford a white solid. This material was subjected to radial chromatography on a 4 mm plate eluting with 20% (v/v) acetone in dichloromethane. These procedures afforded 113 mg (ca. 100%) of the chloroformate, 4-(4-(5-((acetylamino)methyl)-2-oxo- 3-oxazolidinyl)-2-fluorophenyl)-1-piperazinecarboxylic acid, 2-hydroxyethyl ester, as a white solid, mp=121°–123° C. A solution of this material in 5 ml methanol was treated with 35 mg 10% palladium on carbon followed by hydrogenolysis at 1 atmosphere for 1 hour. The mixture was filtered through celite, washing the filter cake with methanol. The filtrate was concentrated in vacuo to afford a white solid. This material was subjected to radial chromatography on a 2 mm plate, eluting with 5% (v/v) methanol in chloroform, and then with 10% (v/v) methanol in chloroform. These procedures afforded 76 mg (82%) of the hydroxyethyl chloroformate 4-(4-(5-((acetylamino)methyl)-2-oxo-3-oxazolidinyl)-2-fluorophenyl) -1-piperazinecarboxylic acid, 2-hydroxyethyl ester as a white solid, mp=203°–206° C.

EXAMPLE 7

N-((3-(4-(3-Fluoro-4-((benzoyl)-1-piperazinyl))phenyl)-2-oxo-5-oxazolidinyl)methyl)-acetamide Following the procedure of Example 1, the subject compound, was prepared from 100 mg (0.297 mmol) of N-((3-(4-(3-fluoro-4-(1-piperazinyl))phenyl)-2-oxo- 5-oxazolidinyl)methyl)-acetamide (22) (Ex. 1, Part k.) substituting benzoyl chloride for the starting material methyl chloroformate. These procedures afforded 73 mg (56%) of N-((3-(4-(3-Fluoro-4-((phenylcarbonyl)- 1-piperazinyl))phenyl)-2-oxo-5-oxazolidinyl)methyl)-acetamide as a fine white powder, mp=184°–187° C.

EXAMPLE 8

4-[4-[5-[(acetylamino)methyl]-2-oxo-3-oxazolidinyl]-
2-fluorophenyl]-1-piperazinecarboxylic acid,
2-methoxyethyl ester A solution of 75 mg (0.22 mmol) of piperazine derivative 22 in 4 mL acetone and 2 mL water was treated with 21 mg (0.25 mmol) sodium bicarbonate followed by cooling to 0° C. and addition of a solution of 35 mg (0.25 mmol) of 2-methoxyethyl chloroformate in 0.5 mL tetrahydrofuran. The mixture was warmed to ambient temperature for 22 hours. The mixture was diluted with 30 mL ethyl acetate and was extracted with water (3×20 mL) and saturated sodium bicarbonate solution (20 mL). The combined aqueous layers were extracted with ethyl acetate (2×20 mL) and the combined organic layers were dried ($Na_2SO_4$) and concentrated in vacuo to afford a white solid. This material was subjected to radial chromatography on a 4 mm plate eluting initially with 20% (v/v) acetone in dichloromethane and then with 30% (v/v) acetone in dichloromethane. These procedures afforded 92 mg (96%) of the desired compound as a white solid.

EXAMPLE 9

4-[4-[5(acetylamino)methyl]-2-oxo-3-oxazolidinyl]-2-
fluorophenyl]-1-piperazineacetonitrile A solution of 75 mg (0.22 mmol) of piperazine derivative 22 in 4 mL acetone and 2 mL water was treated with 21 mg (0.25 mmol) sodium bicarbonate, followed by cooling to 0° C. The mixture was treated with 226 mg (190 μL, 3.0 mmol) of freshly distilled chloroacetonitrile followed by warming to ambient temperature for 60 hours. The solution was diluted with 35 mL ethyl acetate and extracted with water (3×20 mL) and saturated sodium bicarbonate solution (20 mL). The combined aqueous layers were extracted with ethyl acetate (3×20 mL) and the combined organic layers were dried ($Na_2SO_4$) and concentrated in vacuo to afford a white solid. This material was subjected to radial chromatography on a 4 mm plate eluting with 5% (v/v) methanol in chloroform. These procedures afforded 80 mg (96%) of the desired nitrile as a shiny white solid.

EXAMPLE 10

(+/−)-N-[[3-[4-[4-(1,4-Dioxopentyl)-1-piperazinyl]-
3-fluorophenyl]-2-oxo-5-oxazolidinyl]methyl)
Acetamide (Y=$MeCO(CH_2)_2CO$—, monoF,
racemic)

The compound of Ex. 1(k), above, (0.104 g) was treated with 0.041 g of levulinic acid, 0.083 g of 1-ethyl-3-(3-dimethylaminopropyl)carbodiimide, and 0.005 g of N,N-dimethylaminopyridine in 2 mL of pyridine, and the mixture stirred for 2 days at 20° C. Following aqueous extractive workup using methylene chloride, 0.139 g of residue was obtained. This was purified using medium pressure liquid chromatography on silica gel, 5% methanol in ethyl acetate (v/v), to give 0.118 g of a white solid, mp 148°–150° C.

EXAMPLE 11

N-[[3-[4-[4-(1,4-Dioxopentyl)-1-piperazinyl]-3,5-
difluorophenyl]-2-oxo-5-oxazolidinyl]methyl)
Acetamide, (S)—(Y=same as above, diF, optically
active)

Using the same general procedure as in the above procedure to make Example 10, but starting with the trifluoroacetate salt of piperazine U-99472, prepared as directly below, 0.291 g of the salt gave after medium pressure liquid chromatography followed by preparative TLC (1000 μm, 20% acetone/methylene chloride, v/v) to give 0.103 g of a foamy white solid, mp 52°–56° C.

EXAMPLE 12

(+/−)-N-[[3-[4-[4-[(1-Oxo-6-oxa-7-phenyl)heptyl]-1-
piperazinyl]-3-fluorophenyl]-
2-oxo-5-oxazolidinyl]methyl) Acetamide
(Y=$PhCH_2O(CH_2)_4CO$—)

Following the general procedure of above for Example 10, but substituting 5-benzyloxyvaleric acid (0.074 g) for the levulinic acid, 0.101 g of the compound of Ex. 1k, above, gave after medium pressure liquid chromatography (10% methanol in ethyl acetate) 0.130 g of the title compound, tlc $R_f$=0.24 (10% methanol in ethyl acetate, v/v).

EXAMPLE 13

(+/−)-N-[[3-[4-[4-(1-Oxo-5-hydroxypentyl)-
1-piperazinyl]-3-fluorophenyl]-2-oxo-
5-oxazolidinyl]methyl) Acetamide
(Y=$HO(CH_2)_4CO$—)

The compound of Example 12, (66 mg) was dissolved in 5 mL of methanol, and the flask evacuated and filled with nitrogen 3 times. To the mixture was added 0.034 g of palladium black, and the flask evacuated and filled with hydrogen from a balloon 3 times. The mixture was stirred under hydrogen for 3 hr, then filtered through diatomaceous earth and washed with methanol, and the filtrate was evaporated. This residue was triturated with chloroform and and a white solid precipitated, this was collected to give the titled compound, tlc $R_f$=0.07 (10% methanol in ethyl acetate, v/v), 171–172 C m.p.

EXAMPLE 14

N-[[3-[3,5-Difluoro-4-[4-[5-R,S-methyl-
[(1,3-dioxa-2-oxo)cyclopentyl]]]-1-piperazinyl]phenyl)-
2-oxo-5-oxazolidinyl]methyl]Acetamide, —(5S)
(Y=cyclic carbonate, optically active at
oxazolidinone, but has racemate at cyclic
carbonate, diF)

A BOC-piperazine, diF, optically active compound (0.094 g) was treated with 1.0 mL of trifluoroacetic acid in 1.5 mL of methylene chloride at 0° C. for 50 min, then allowed to warm to 20° C., and the volatiles removed in vacuo to give a red oil (trifluoroacetate of U-99472). To this was added 0.036 g of chloromethylethylene carbonate and 0.069 g of potassium carbonate in acetonitrile, and the mixture heatd at reflux for one day. The mixture was filtered and evaporated in vacuo to give a yellow oil. The residue was purified by medium pressure liquid chromatography on silica gel (gradient elution with 5%–10% methanol in methylene chloride (v/v), followed by prepative TLC (7% methanol in methylene chloride) to give 0.022 g of a white solid, mp 106°–111° C.

EXAMPLE 15

N-[[3-[3,5-Difluoro-4-[4-(1-oxo-2-methoxyethyl)-
1-piperazinyl]phenyl]-2-oxo-5-oxazolidinyl]methyl]-
Acetamide, (S)—(Y=$MeOCH_2CO$-optically active,
diF)

To a solution of the trifluoroacetate salt of piperazine (0.192 g) in 3 mL of methylene chloride and 1.0 mL of triethylamine under nitrogen at 0° C. was added 0.071 g of methoxyacetyl chloride. The mixture was stirred at 0° C., then worked up by aqueous extraction using methylene chloride. The organic layer was dried (MgSO$^4$) and concentrated to 5–10 mL, and cooled, the solids were collected and recrystallized from ethyl acetate to give 44 mg of a white solid, mp 239°–241° C.

EXAMPLE 16

(+/−)-N-[[3-[4-[4-(N-carbobenzyloxy)-2-amino-1-oxo-ethyl)-1-piperazinyl]]-3-fluorophenyl]-2-oxo-5-oxazolidinyl]methyl]Acetamide
(Y=PhCH$_2$O$_2$CNHCH$_2$CO— racemic, monoF)

To the compound of Ex. 1k (0.115 g) was added 0.085 g of N-carbobenzyloxyglycine in 4 mL of tetrahydrofuran and 2 mL of water, then the pH was adjusted to about 4 with the addition of 3N hydrochloric acid, the 0.203 g of 1-ethyl-3-(3-dimethylaminopropyl) carbodiimide was added. The mixture was stirred at 20° C. for 1 hr, then additional 0.101 g of N-carbobenzyloxyglycine and 0.225 g of 1-ethyl-3-(3-dimethylaminopropyl) carbodiimide were added, and the pJ was adjusted from 3 to between 4 and 5 with the addition of 2N sodium hydroxide, and the mixture stirred overnight. After extractive aqueous workup with ethyl acetate, the organic layers were concentrated and the residue was purified by concentration from methylene chloride and methanol, then trituration with methanol to give 0.042 mg of a white solid, mp=189°–191° C.

EXAMPLE 17

(S)-N-[[3-[4-[4-(cyanomethyl)-1-piperazinyl]-3-fluorophenyl]-2-oxo-5-oxazolidinyl]methyl-acetamide: (U-97665)

The following steps demostrate the preparation of a mono-F substituted product of the invention.
(a) (S)-4-[4-[5-(hydroxymethyl)-2-oxo-3-oxazolidinyl]-2-fluorophenyl]-1-piperazinecarboxylic acid, 1,1-dimethylethyl ester (2):

A solution of 7.5g (17.5 mmol) of the CBz derivative 1 in 240 ml of tetrahydrofuran at −78° C. was treated with 12.0 mL (1.6M, 19.25 mmol) of n-butyllithium in hexane dropwise over ca. 3 min. The solution was stirred at −78° C. for 30 min, followed by addition of 2.78 g (2.73 mL, 19.25 mmol) of neat R-(−)-glycidyl butyrate dropwise over ca. 5 min followed by warming of the solution to 0° C. and then eventually to ambient temperature for 18 h. The mixture was diluted with dichloromethane and extracted with water and saturated aqueous sodium chloride solution. The organic layer was dried (Na$_2$SO$_4$) and concentrated in vacuo to afford a gummy residue. This material was recrystallized from hot ethyl acetate with some hexane added, to afford 6.4 g (93%) of the desired product, mp 130.5°–133° C.

(b) (S)-4-[4-[5-(methanesulfonyloxymethyl)-2-oxo-3-oxazolidinyl]- 2-fluorophenyl]-1-piperazinecarboxylic acid, 1,1-dimethylethyl ester (3):

A solution of 2.88 g (7.28 mmol) of the alcohol 2 in 32 mL dichloromethane at 0° C. was treated with 1.29 g (1.77 mL, 12.7 mmol) of triethylamine followed by addition of 1.04 g (0.70 mL, 9.10 mmol) of methanesulfonylchloride. The solution was stirred at 0° C. for 15 min, followed by dilution with dichloromethane and extraction with water. The solution was dried (Na$_2$SO$_4$) and concentrated in vacuo to afford 3.4 g (98%) of the mesylate 3 as a light pink solid (high resolution mass spectrum: calcd for C$^{20}$H$^{28}$FN$^3$O$^7$S: 473.1632. found: 473.1631), sufficiently pure for use in the next step.

(c) (S)-4-[4-[5-(azidomethyl)-2-oxo-3-oxazolidinyl]-2-fluorophenyl]-1-piperazinecarboxylic acid, 1,1-dimethylethyl ester (4):

A solution of the 16.8 g (35.5 mmol) of the mesylate 3 in 400 mL of dimethylformamide was treated with 11.5 g (177.5 mmol) of sodium azide followed by warming at 60° C. for 16 h. The solution was diluted with ethyl acetate and extracted with water. The organic layer was dried (Na$_2$SO$_4$) and concentrated in vacuo to afford 14.9 g (100%) of the azide 4 as a light yellow solid, mp 101°–104° C., sufficiently pure for further use.

(d) (S)-4-[4-[5-[(acetylamino)methyl]-2-oxo-3-oxazolidinyl]-2-fluorophenyl]-1-piperazinecarboxylic acid, 1,1-dimethylethyl ester (5):

A solution of 14.92 g (35.5 mmol) of the azide 4 in 2000 mL of ethyl acetate was treated with 2 g of 10% palladium on carbon followed by hydrogenation at one atmosphere for 24 h. The flask was flushed with nitrogen, followed by sequential addition of 14.0 g (14.4 ml, 177.5 mmol) of pyridine and 9.1 g (8.4 mL, 88.8 mmol) of acetic anhydride. The mixture was stirred at ambient temperature for 72 h, followed by filtration through celite. The filtrate was extracted with water, 1N copper sulfate solution, dried and concentrated in vacuo to afford a tan solid. This material was purified by silica gel chromatography to afford 12.7 g (82%) of the product 5 as a powdery white solid, mp 153°–159° C.

(e) (S)-N-[[3-[4-[3-fluoro-4-(1-piperazinyl)]phenyl]-2-oxo-5-oxazoldinyl]methyl]-acetamide:

35 mL of trifluoroacetic acid at 0° C. was treated with 5.0 g (11.46 mmol) of the Boc-derivative followed by warming to ambient temperature over 1 h. The solution was concentrated in vacuo to afford a residue which was dissolved in water and stirred with 125 mL of AG1-X8 (OH$^-$ form) ion exchange resin for 2.5 h. The resin was removed by filtration, washed with water, and the combined filtrates were freeze-dried to afford 2.7 g (69%) of the desired title compound as a white fluffy solid, mp 73°–76° C.

(f) (S)-N-[[3-[4-[4-(cyanomethyl)-1-piperazinyl]-3-fluorophenyl]-2-oxo-5-oxazolidinyl]methyl-acetamide A solution of 2.42 g (7.2 mmol) of the above compound (e) in 242 mL acetone and 74 mL water was cooled to 0° C. and treated with 1.20 g (14.4 mmol) of sodium bicarbonate, followed by addition of 26.2 g (22.0 mL, 0.35 mol) of chloroacetonitrile. The solution was then warmed to ambient temperature for 36 h. The mixture was then diluted with ethyl acetate and extracted with water and saturated sodium chloride solution. Drying (Na$_2$SO$_4$) and concentration in vacuo afforded and off-white solid which was purified by silica gel chromatography eluting with a methanol-chloroform solvent system. These procedures afforded 2.2 g (82%) of the title compound as a fluffy white solid, mp 166°–167° C.

EXAMPLE 18

(S)-N-[[3-[4-[4-(cyanomethyl)-1-piperazinyl]-3,5-difluorophenyl]-2-oxo-5-oxazolidinyl]methyl-acetamide Following the procedure for preparation of Example 17, substituting difluoro piperazine derivative ((S)-N-[[3-[3,5-difluoro-4-(1-piperazinyl)phenyl]-2-oxo-5-5oxazolidinyl]methyl-acetamide) for monofluoro derivative Ex. 17(e), the title compound was obtained as a white powder, mp 150°–154° C.

EXAMPLE 19

(+)-N-[[3-[4-[4-(2-cyanoethyl)-1-piperazinyl]-3-fluorophenyl]-2-oxo-5-oxalidinyl]methyl]-acetamide A solution of 75mg (0.22 mmol) of a racemic of Ex. 17(e) in 5 mL methanol was treated with 13 mg (17 μL, 0.25 mmol) of acrylonitrile followed by warming at reflux for 3 h. The solution was concentrated in vacuo. The residue was subjected to radial chromatography eluting with 5% (v/v) methanol in chloroform. These procedures afforded 84 mg (97%) of the title compound as a white solid, mp 125°–130° C.

EXAMPLE 20

(+)-N-[[3-[4-[4-(2-cyano-2-propyl)-1-piperazinyl]-3-fluorophenyl]-2-oxo-5-oxazolidinyl]-methyl-acetamide A solution of 75 mg (0.22 mmol) of racemic Ex. 17(e) in 1 mL dry acetonitrile was treated sequentially with 5 mg (0.03 mmol) anhydrous zinc chloride, 26 mg (331 μL, 0.45 mmol) dry acetone, and 44 mg (591 μL, 0.45 mmol) trimethylsilylcyanide. The solution was warmed at reflux for 18 h, followed by dilution with ethyl acetate and extraction with water. Drying (Na$_2$SO$_4$) and concentration in vacuo afforded a tan solid which was subjected to radial chromatography eluting with 5% (v/v) methanol in dichloromethane. These procedures afforded 36 mg (40%) of the title compound as a white solid, mp 139°–143° C.

EXAMPLE 21

(S)-N-[[3-[4-[4-(4-cyanotetrahydropyran-4-yl)-1-piperazinyl]-3-fluorophenyl]-2-oxo-5-oxazolidinyl]-methyl-acetamide A solution of 50 mg (0.15 mmol) of Ex. 17(e) in 2 mL dry acetonitrile was treated sequentially with 3 mg (0.02 mmol) anhydrous zinc chloride, 30 mg (281 μL, 0.30 mmol) tetrahydropyran-4-one, and 29 mg (40 μL, 0.30 mmol) trimethylsilylcyanide. The solution was warmed at reflux for 30 h, followed by dilution with ethyl acetate and extraction with water. Drying (Na$_2$SO$_4$) and concentration in vacuo afforded a light yellow solid. This material was subjected to radial chromatography eluting with a methanol-dichloromethane solvent system. These procedures afforded 24 mg (36%) of the title compound as a white solid, mp 134°–137° C.

EXAMPLE 22

(±)-N-[[3-[3-fluoro-4-(4-formyl-1-piperazinyl)phenyl]-2-oxo-5-oxazolidinyl]methyl]-Acetamide A solution of 0.250 g (0.267 mmol) of racemice Ex. 17(e) in 4 mL THF and 2 mL water was treated with 11 mg (91 μL, 0.243 mmol) of formic acid and adjusted to pH 4.5 using 0.1N aqueous hydrochloric acid. The mixture was then added at once to 153 mg (0.80 mmol) of 1-ethyl- 3-(3-dimethylaminopropyl)carbodiimide hydrochloride in 1 mL water with stirring at ambient temperature and the mixture adjusted to pH 4.5 using 2N sodium hydroxide and 0.1N hydrochloric acid. After stirring about 1 hour, additional carbodiimide (100 mg, 0.53 mmol) and formic acid (30 mg, 0.80 mmol) were added with stirring at ambient temperature for 16 h. The mixture was diluted with water and extracted with ethyl acetate. The organic layer was subsequently extracted with saturated sodium bicarbonate and saturated sodium chloride solutions, dried (Na$_2$SO$_4$) and concentrated in vacuo to afford a white solid. This material was subjected to silica gel chromatography eluting with a methanol-methylene chloride system to afford 0.094 g (97%) of the title compound as a white solid, mp 190°–193.5° C.

EXAMPLE 23

(S)-4-[4-[5-[(Acetylamino)methyl]-2-oxo-3-oxazolidine)]-2-fluorophenyl]-1-piperazinecarboxylic acid methyl ester A solution of Ex. 17(e) in 22 mL acetone and 11 mL water was treated with 150 mg (1.80 mmol) of sodium bicarbonate and cooled to 0° C. followed by addition of 0.170 g (0.14 mL, 1.80 mmol) of methyl chloroformate. After 2 h, the mixture was diluted with ethyl acetate and extracted with water and saturated sodium chloride solution. Drying (Na$_2$SO$_4$) and concentration in vacuo afforded a white solid which was purified by silica gel chromatography eluting with an acetone-methylene chloride system. These procedures afforded 0.494 g (77%) of the title compound as white solid, mp 179.5°–182° C.

EXAMPLE 24

(S)-4-[4-[5-[(Acetylamino)methyl]-2-oxo-3-oxazolidine)]-2,6-difluorophenyl]-1-piperazinecarboxylic acid methyl ester Following the procedure for preparation of Ex. 23, substituting difluoropiperazine 7 for Ex. 17(e), the title compound was obtained as a white powder, mp 175°–178° C.

EXAMPLE 25

(±)-N-[[3-[4-[3-fluoro-4-[(phenylcarbonyl)-1-piperazinyl]]phenyl]-2-oxo-5-oxazolidinyl]-methyl]-acetamide Following the procedure for preparation of Ex. 23 (using racemic Ex. 17(e), and substituting benzoyl chloride for methyl chloroformate, the title compound was obtained as a white powder, mp 184°–187° C.

EXAMPLE 26

(±)-4-[4-[5-[(Acetylamino)methyl]-2-oxo-3-oxazolidine)]-2-fluorophenyl]-1-piperazinecarboxylic acid, 2-methoxyethyl ester A solution of 75 mg (0.22 mmol) of monofluropiperazine derivative Ex. 25 in 4 mL acetone and 2 mL water was treated with 21 mg (0.25 mmol) of sodium bicarbonate followed by cooling to 0° C. The solution was the treated with a solution of 35 mg (0.25 mmol) of 2-methoxyethyl chloroformate in 0.5 mL tetrahydrofuran. The solution was then warmed to ambient temperature for 22 h. The solution was diluted with ethyl acetate and extracted with water, saturated sodium bicarbonate solution, and saturated sodium chloride solution. The organic layer was dried (Na$_2$SO$_4$) and concentrated in vacuo to afford a white solid. This material was subjected to radial chromatography eluting with an 30% (v/v) acetonedichloromethane. These procedures afforded 92 mg (96%) of the title compound as a white solid, mp 166°–167° C.

EXAMPLE 27

(S)-4-[4-[5-[(Acetylamino)methyl]-2-oxo-3-oxazolidine)]2,6-difluorophenyl]-1-piperazinecarboxylic acid, 2-methoxyethyl ester Following the procedure for the preparation of Ex. 26, substituting difluoropiperazine 7 for Ex. 17(e), the title compound was obtained as a white solid, mp 154.5°–156° C.

EXAMPLE 28

(±)-4-[4-[5-[(acetylamino)methyl]-2-oxo-3-oxazolinyl-2-fluorophenyl]-1-piperazinecarboxylic acid, 2-(phenylmethoxy)ethyl ester A solution of 208 mg (0.25 mmol) of Ex. 25 in 3 mL acetone and 2 mL water was treated with 21 mg (0.25 mmol) of sodium bicarbonate followed by cooling to 0° C. The mixture was treated with a solution of 54 mg (0.25 mmol) of 2-(phenylmethoxy)ethyl chloroformate in 2 mL acetone. The solution was warmed to ambient temperature for 22 h, followed by dilution with ethyl acetate and extraction with water and saturated sodium bicarbonate solution. Drying ($Na_2SO_4$) and concentration in vacuo afforded a white solid which was subjected to radial chromatography eluting with 20% (v/v) acetone in dichloromethane. These procedures afforded 113 mg (100%) of the title compound as a white solid, mp 121°–123° C.

EXAMPLE 29

(S)-4-[4-[5-[(acetylamino)methyl]-2-oxo-3-oxazolinyl-2,6-difluorophenyl]-1-piperazinecarboxylic acid, 2-(phenylmethoxy)ethyl ester Following the procedure for preparation of Ex. 28, substituting difluoropiperazine 7 for Ex. 17(e), the title compound was obtained as a white solid, mp 108°–110° C.

EXAMPLE 30

(±)-4-[4-[5-[(acetylamino)methyl]-2-oxo-3-oxazolinyl-2,6-difluorophenyl]-1-piperazinecarboxylic acid, 2-hydroxyethyl ester A solution of 113 mg of Ex. 28 in 5 mL methanol was treated with 35 mg 10% palladium on carbon followed by hydrogenation at atmospheric pressure for 1 h. The mixture was faltered through celite, washing the filter cake with methanol. The filtrate was concentrated in vacuo to afford a white solid. This material was purified by radial chromatography eluting with a methanol-chloroform solvent system. These procedures afforded 76 mg (82%) of the title compound as a white solid, mp 203°–206° C.

EXAMPLE 31

[S-(R )]-N-[[3-[3,5-difluoro-4-[4-[(tetrahydro-2-furanyl)carbonyl]-1-piperazinyl]phenyl]-2-oxo-5-oxazolidinyl]methyl]-acetamide A solution of 100 mg (0.28 mmol) of difluoropiperazine derivative ((S)-N-[[3-[3,5-difluoro- 4-(1-piperazinyl)phenyl]-2-oxo-5-5oxazolidinyl]methyl-acetamide) and 144 mg (1.25 mmol) of (R)-2-tetrahydorfuranoic acid in 4 mL tetrahydrofuran and 2 mL water was adjusted to pH 4.5 by addition of 2N NaOH solution. This solution was treated with a solution of 324 mg (1.69 mmol) of 1-ethyl-3-(3-dimethylaminopropyl)carbodiimide hydrochloride in 2 mL water. The solution was then maintained at pH 4.6 by addition of 2N NaOH solution while stirring at ambient temperature for 1.5 h. The solution was diluted with water and extracted with ethyl acetate. The combined organic layers were dried ($Na_2SO_4$) and concentrated in vacuo to afford a tan solid which was subjected to radial chromatography eluting with a methanol-dichloromethane solvent system. These procedures afforded 106 mg (83%) of the title compound amide as a white solid, mp 198°–200° C.

EXAMPLE 32

(S)-N-[[3-[3,5-difluoro-4-[4-[2-(1-piperidinyl)ethyl]-1-piperazinyl]phenyl]-2-oxo-5-oxazolidinyl]methyl]acetamide The following demonstrates the preparation steps for difluorointermediates of the invention.

(a) 2,6-difluoro-4-nitrobenzene(trifluoromethane)sulfonate.

2,6-Difluoro-4-nitrophenol (31.55 g, 180.19 mmol) was combined with $CH_2Cl_2$ (300 mL) and pyridine (29.15 mL, 360.38 mmol). The resultant slurry was cooled to 0° C. in an ice bath and then treated dropwise with triflic anhydride (31.8 mL, 189.2 mmol) over a period of 45 minutes. The reaction was allowed to stir at 0 ° C. for two hours and then it was stored in the refrigerator (5° C.) overnight. The reaction was determined to be complete by TLC (15% EtOAc/hexane, UV short wave). The reaction mixture was concentrated under reduced pressure, and then treated with both $H_2O$ (50 mL) and EtOAc (50 mL). This mixture was transferred to a separatory funnel with more EtOAc (100 mL) and washed with 1N HCl until the washings were acidic (2×100 mL). The aqueous phases were back-extracted with EtOAc (2×200 mL). The combined EtOAc extracts were combined and then washed again with 1N HCl (400 mL) and once with brine (400 mL). The organic phase was dried over anhydrous $Na_2SO_4$, filtered and then concentrated to yield 54.092 g of a red-gold oil. Although the oil was pure by NMR, it was combined with crude products from two other runs and chromatographed over silica gel (550 g) packed with 5% EtOAc. Elution with 2 L each of 5% EtOAc and 10% EtOAc afforded a 95% overall yield of the title compound as a pale yellow oil with HRMS ($M^+$) calcd for $C_7H_2F_5NO_5S$ 306.9574, found 306.9590.

(b) 1-(tert-butoxycarbonyl)-4-(2,6-difluoro-4-nitrophenyl)piperazine.

A solution of 2,6-difluoro-4-nitrobenzene(trifluoromethane)sulfonate (55 g, 179 mmol) in dry DMF (275 mL) was treated with 1-(tert-butoxycarbonyl)piperazine (45.71 g, 250 mmol). The resultant clear yellow solution turned orange upon the addition of N,N-diisopropylethylamine (47 mL, 269 mmol). The reaction was heated to reflux for 15 hours under $N_2$. The reaction was determined to be complete by TLC (30% EtOAc/hexane, UV short wave). The reaction mixture was concentrated to dryness and combined with the crude product of another reaction for purification. The crude material was dissolved in hot $CH_2Cl_2$ (420 mL; some solids unrelated to the product did not dissolve) and then chromatographed on three separate columns (2 columns with 750 g silica gel, packed with $CH_2Cl_2$, loaded with 180 mL material, and eluted with 1 L each of 1–5% EtOAc/$CH_2Cl_2$; one column with 250 g silica gel, packed with $CH_2Cl_2$, loaded with 60 mL compound, and eluted with 2.5 and 5% EtOAc/$CH_2Cl_2$) to give an 87% yield of the title compound as an orange solid with HRMS ($M^+$) calcd for $C_{15}H_{19}F_2N_3O_4$ 343.1343, found 343.1358.

(c) 1-(tert-butoxycarbonyl)-4-[2,6-difluoro-4-(benzyloxycarbonyl)aminophenyl]piperazine.

The 1-(tert-butoxycarbonyl)-4-(2,6-difluoro-4-nitrophenyl)piperazine (44.7 g, 130 mmol) was dissolved in 20% THF/MeOH (600 mL) in a 2 L flask. Ammonium formate (41 g, 651 mmol) was added portionwise, followed by 10% Pd-C (1.12 g, 2.5 weight %), with cooling in an ice bath. When the addition was completed the ice bath was removed. The flask became slightly warm, and the yellow color disappeared. The reaction was found to be complete by TLC (30% EtOAc/hexane, UV short wave) in 1.5 hours. The reaction mixture was filtered through Celite (washing the filter cake with 500 mL MeOH). The filtrate was concentrated under reduced pressure to give a solid which was then treated with 1 L EtOAc and 500 mL $H_2O$. The layers were separated and then the organic layer was washed again with $H_2O$ (500 mL) and once with brine (500 mL). The aqueous portions were back-extracted with more EtOAc (2×300 mL). The combined organic extracts were dried over anhydrous $Na_2SO_4$, filtered and concentrated to yield a yellow solid (40.8 g) which was immediately dissolved in dry DMF (500 mL) and cooled to −20 ° C. (ice/MeOH bath) under $N_2$. The solution was treated with N,N-dimethylaniline (20.6 mL, 163 mmol), followed by the dropwise addition of of benzyl chloroformate (21.5 mL, 143 mmol). The ice bath was allowed to dissipate overnight. The reaction was determined to be complete by TLC (30% EtOAc/hexane, UV short wave). The mixture was concentrated down to a yellow oil, dissolved in 1 L of EtOAc, and washed with $H_2O$ (500 mL) and brine (500 mL). The aqueous portions were back-extracted with more EtOAc (2×300 mL). The combined organic extracts were dried over anhydrous $Na_2SO_4$, filtered and concentrated to yield a yellow solid. The crude material was recrystallized from hot EtOAc/hexane to afford 39.11 g (67%) of the title compound as a pale yellow crystalline solid with mp 171°–172° C.

(d) [3-[3,5-difluoro-4-[4-(tert-butoxycarbonyl)-1-piperazinyl]phenyl]-2-oxo-5oxazolidinyl]methanol.

The 1-(tert-butoxycarbonyl)-4-[2,6-difluoro-4-(benzyloxycarbonyl)aminophenyl]piperazine (14.05 g, 31 mmol) was dissolved in dry THF (150 mL) and then cooled to −78° C. (dry ice/acetone). The reaction was next treated with with n-BuLi (21.6 mL, 35 mmol) dropwise over a 25 minute period. The reaction was allowed to stir at −78° C. for 30 minutes and then (R)-(−)-glycidylbutyrate (4.89 mL, 35 mmol) was added dropwise over 7 minutes. The reaction was maintained at −78° C. for an additional 15 minutes and then the bath was removed, allowing the reaction to slowly warm up to room temperature overnight. The reaction was determined to be complete by TLC (5% MeOH/CHCl$_3$, UV short wave). The reaction mixture was diluted with 500 mL $CH_2Cl_2$ and then washed with both $H_2O$ (3×300 mL) and brine (300 mL). The aqueous portions were back-extracted with more $CH_2Cl_2$ (3×400 mL). The combined organic extracts were dried over $Na_2SO_4$, filtered and concentrated to give a creamy yellow solid. The crude solid was purified by recrystallization from hot EtOAc/hexane to give 11.063 g (85%) of the title compound as a white solid with mp 164°–166° C.

(e) [[3-[3,5-difluoro-4-[4-(tert-butoxycarbonyl)-1-piperazinyl]phenyl]- 2-oxo-5-oxazolidinyl]methyl]-p-toluenesulfonate.

The [3-[3,5-difluoro-4-[4-(tert-butoxycarbonyl)-1-piperazinyl]phenyl]-2-oxo-5-oxazolidinyl]methanol (24.2 g, 59 mmol) was dissolved in pyridine (110 mL) and then cooled to 0° C. (ice bath). Freshly recrystalized p-toluenesulfonyl chloride (13.4 g, 70 mmol) of was added and the reaction was allowed to stir at 0° C. for 2.5 hours under $N_2$. The flask was then stoppered and stored in the refrigerator (5° C.) overnight. The reaction mixture became a pale pink slurry. TLC revealed that some alcohol still remained. The reaction mixture was treated with additional p-toluenesulfonyl chloride (1.12 g, 5.85 mmol), catalytic 4-(dimethylamino)pyridine, and 20 mL of dry $CH_2Cl_2$ to facilitate stirring. After 4 hours at 0° C., the reaction was found to be complete by TLC (5% MeOH/CH$_2$Cl$_3$, UV short wave). The mixture was added to 750 mL ice water and the precipitated product isolated via suction filtration, washing it with both water (1 L) and ether (500 mL). After drying in vacuo, 29.921 g (90%) of the title compound was obtained as white solid with mp 150.5°–151.5 ° C.

(f) [[3-[3,5-difluoro-4-[4-(tert-butoxycarbonyl)-1-piperazinyl]phenyl]-2-oxo-5-oxazolidinyl]methyl]methanesulfonate.

The [3-[3,5-difluoro-4-[4-(tert-butoxycarbonyl)-1-piperazinyl]phenyl]-2-oxo-5-oxazolidinyl]methanol (3.831 g, 9.27 mmol) was dissolved in $CH_2Cl_2$ (40 mL), cooled to 0° C., and treated with triethylamine (1.74 g, 2.4 mL, 17.22 mmol) under $N_2$. Methanesulfonyl chloride (1.48 g, 1 mL, 12.92 mmol) was slowly added over 1 min. TLC analysis (20% acetone/$CH_2Cl_2$) after 0.5 h revealed the reaction to be complete. The reaction mixture was diluted with $CH_2Cl_2$ (200 mL) and washed with water (3×50 mL) and brine (50 mL), dried over $Na_2SO_4$, filtered and concentrated in vacuo to furnish the title compound as an off-white solid with HRMS (M$^+$) calcd for $C_{20}H_{27}F_2N_3O_7S$ 491.1538, found 491.1543.

(g) [[3-[3,5-difluoro-4-[4-(tert-butoxycarbonyl)-1-piperazinyl]phenyl]-2-oxo-5-oxazolidinyl]methyl]azide.

The [[3-[3,5-difluoro-4-[4-(tert-butoxycarbonyl)-1-piperazinyl]phenyl]-2-oxo-5-oxazolidinyl]methyl]-p-toluenesulfonate (29.661 g, 52 mmol) was dissolved in dry DMF (125 mL) and then treated with solid NaN$_3$ (10.19 g, 156 mmol) at room temperature. The reaction was heated to 60° C. for three hours and then allowed to cool to room temperature overnight under $N_2$. The reaction was found to be complete by TLC (30% EtOAc/hexane, run twice, UV short wave). The reaction mixture was concentrated in vacuo to give a cream colored solid. The crude product was dissolved in 600 mL EtOAc and then washed with both $H_2O$ (2×500 mL) and brine (500 mL). The aqueous portions were back-extracted with more EtOAc (2×400 mL). The combined organic extracts were dried over $Na_2SO_4$, filtered and concentrated in vacuo to yield 22.41 g (91%) of the title compound as a pale yellow solid with mp 115°–117° C.

Employing essentially identical conditions, the corresponding mesylate was converted to the same azide.

(h) N-[[3-[3,5-difluoro-4-[4-(tert-butoxycarbonyl) -1-piperazinyl]phenyl]-2-oxo-5-oxazolidinyl]methyl]acetamide.

The [[3-[3,5-difluoro-4-[4-(tert-butoxycarbonyl)-1-piperazinyl]phenyl]-2-oxo-5-oxazolidinyl]methyl]azide (22.4 g, 51 mmol) was dissolved in 1 L of EtOAc and then degassed three times with $N_2$. Next, 10% Pd-C (4.48 g, 20% by weight) was added and the solution was degassed again three times (with $N_2$) before replacing the atmosphere with $H_2$ (balloon). After hours, the reaction was determined to be complete by TLC (20% MeOH/CHCl$_3$, UV short wave). At this point, pyridine (8.25 mL, 102 mmol) was added, followed by treatment with acetic anhydride (9.54 mL, 102 mmol). The reaction mixture was allowed to stir overnight at room temperature. The reaction was found to be complete by TLC (20% MeOH/CHCl$_3$, UV short wave). The reaction mixture was filtered through celite (the filter cake was washed with 500 mL EtOAc), the filtrate concentrated down to approximately 600 mL, and washed with $H_2O$ (2×500 mL) and brine (500 mL). The aqueous portions were back-extracted with more EtOAc (2×500 mL). The combined organic extracts were dried over anhydrous $Na_2SO_4$, filtered and concentrated to give a yellow solid. Recrystallization of the crude product from hot $CHCl_3$ and hexane afforded 19.157 g (83%) of the title compound as a white solid with mp 177°–179° C.

(i) N-[[3-[3,5-difluoro-4-(1-piperazinyl)phenyl]-2-oxo-5-oxazolidinyl]methyl]acetamide.

The N-[[3-[3,5-difluoro-4-[4-( tert-butoxycarbonyl)-1-piperazinyl]phenyl]-2-oxo-5-oxazolidinyl]methyl]acetamide (1.00 g, 2.20 mmol) was dissolved in $CH_2Cl_2$ (6 mL) and cooled to 0° C. with an ice bath. Trifluoroacetic acid (20 mL) was added, the cooling bath removed, and the reaction mixture allowed to warm to ambient temperature over 1 h. The reaction mixture was then concentrated in vacuo and the residue dissolved in $H_2O$ (15 mL). The resultant solution was added to Bio Rad AG-1-X8 ion exchange resin (12 mL; $OH^-$ form, washed with $H_2O$ until neutral), additional $H_2O$ (5 mL) was added, and the mixture stirred for 10 min. The mixture was then filtered and the resin washed with additional $H_2O$ (3×5 mL). The aqueous filtrate was lyophilized to give 0.559 g (72%) of the title compound as a white solid with mp 108°–112° C. (dec).

(j) (S)-N-[[3-[3,5-difluoro-4-[4-[2-(1-piperidinyl)ethyl]-1-piperazinyl]phenyl]-2-oxo-5-oxazolidinyl]methyl]acetamide.

A mixture of (S)-N-[[3-[3,5-difluoro-4-(1-piperazinyl)phenyl]-2-oxo-5-oxazolidinyl]methyl]acetamide (0.200 g, 0.565 mmol), 1-(2-chloroethyl)piperidine monohydrochloride (0.125 g, 0.678 mmol) and potassium carbonate (0.478 g, 3.39 mmol) in acetonitrile (10 mL) was heated to reflux for 1.5 h. The reaction mixture was cooled to ambient temperature and concentrated in vacuo. The residue was triturated with dichloromethane, the solids filtered off, and the filtrate concentrated in vacuo to furnish an off-white solid (0.248 g). This crude material was chromatographed over silica gel (5 g), eluting with 5% and then 10% methanol/chloroform, to afford, after concentration of appropriate fractions, 0.137 g (52%) of the title compound as an off-white solid with mp 198°–200° C.

EXAMPLE 33

(S)-N-[[3-[3-fluoro-4-[4-[2-(1-piperidinyl)ethyl]-1-piperazinyl]phenyl]-2-oxo-5-oxazolidinyl]methyl]-acetamide A mixture of (S)-N-[[3-[3-fluoro-4-(1-piperazinyl)phenyl]-2-oxo- 5oxazolidinyl]methyl]acetamide (0.200 g, 0.595 mmol), 1-(2-chloroethyl)piperidine monohydrochloride (0.131 g, 0.714 mmol) and potassium carbonate (0.493 g, 3.57 mmol) in acetonitrile (12 mL) was heated to reflux for 1.0 h. The reaction mixture was cooled to ambient temperature and concentrated in vacuo. The residue was triturated with dichloromethane, the solids filtered off, and the filtrate concentrated in vacuo to give the crude product (0.308 g). This crude material was chromatographed over silica gel (5 g), eluting with 5% and then 10% methanol/chloroform, to afford, after concentration of appropriate fractions, 0.192 g (72%) of the title compound as an off-white solid with mp 169°–170° C.

EXAMPLE 34

(S)-N-[[3-[3-fluoro-4-[4-[2-(4-morpholinyl)ethyl]-1-piperazinyl]phenyl]-2-oxo-5-oxazolidinyl]methyl]-acetamide A mixture of (S)-N-[[3-[3-fluoro-4-(1-piperazinyl)phenyl]-2-oxo-5-oxazolidinyl]methyl]acetamide (0.200 g, 0.595 mmol), 4-(2-chloroethyl)morpholine hydrochloride (0.133 g, 0.714 mmol) and potassium carbonate (0.493 g, 3.57 mmol) in acetonitrile (12 mL) was heated to reflux for 1.0 h. The reaction mixture was cooled to ambient temperature and concentrated in vacuo. The residue was triturated with dichloromethane, the solids filtered off, and the filtrate concentrated in vacuo to give an amber gum (0.201 g). This crude material was chromatographed over silica gel (5 g), eluting with 5% and then 10% methanol/chloroform, to afford, after concentration of appropriate fractions, 0.129 g (48%) of the title compound as an off-white solid with mp 150°–151.5° C.

EXAMPLE 35

(S)-N-[[3-[4-[4-[2-(diethylamino)ethyl]-1-piperazinyl]-3-fluorophenyl]-2-oxo-5-oxazolidinyl]methyl]acetamide A mixture of (S)-N-[[3-[3-fluoro-4-(1-piperazinyl)phenyl]-2-oxo- 5oxazolidinyl]methyl]acetamide (0.200 g, 0.595 mmol), 2-diethylaminoethyl chloride hydrochloride (0.123 g, 0.714 mmol) and potassium carbonate (0.493 g, 3.57 mmol) in acetonitrile (12 mL) was heated to reflux for 1.0 h. The reaction mixture was cooled to ambient temperature and concentrated in vacuo. The residue was triturated with dichloromethane, the solids filtered off, and the filtrate concentrated in vacuo to give an off-white gummy solid (0.241 g). This crude material was chromatographed over silica gel (5 g), eluting with 5% and then 10% methanol/chloroform, to afford, after concentration of appropriate fractions, 0.159 g (61%) of the title compound as an off-white solid with mp 131°–133° C.

EXAMPLE 36

(S)-N-[[3-[3-fluoro-4-[4-(2-methoxyethyl)-1-piperazinyl]phenyl]-2-oxo-5-oxazolidinyl]methyl]-acetamide A mixture of (S)-N-[[3-[3-fluoro-4-(1-piperazinyl)phenyl]-2-oxo- 5-oxazolidinyl]methyl]acetamide (0.450 g, 1.34 mmol), 2-chloroethyl methyl ether (1.220 mL, 3.40 mmol) and potassium carbonate 1.110 g, 8.04 mmol) in acetonitrile (25 mL) was heated to reflux for 24 h. The reaction mixture was cooled to ambient temperature and concentrated in vacuo. The residue was triturated with dichloromethane, the solids filtered off, and the filtrate concentrated in vacuo to give a yellow foamy solid (0.326 g). This crude material was chromatographed over silica gel (25 g), eluting with 1%, 3%, and then 5% methanol/chloroform, to afford, after concentration of appropriate fractions, 0.296 g (56%) of the title compound as an off-white solid with mp 144.5°–146° C.

EXAMPLE 37

(S)-N-[[3-[3,5-difluoro-4-[4-(2-methoxyethyl)-1-piperazinyl]phenyl]-2-oxo-5-oxazolidinyl]methyl]-acetamide A solution of (S)-N-[[3-[3,5-difluoro-4-[4-(tert-butoxycarbonyl)-1-piperazinyl]phenyl]-2-oxo-5-oxazolidinyl]methyl]acetamide (0.200 g, 0.441 mmol) in dichloromethane (1 mL) was treated with trifluoroacetic acid (4 mL) at room temperature for 1 h. The reaction mixture was concentrated in vacuo and the resultant residue combined with 2-chloroethyl methyl ether (403 μL, 4.41 mmol), potassium carbonate (0.730 g, 5.28 mmol), and acetonitrile (9 mL) and the mixture heated to reflux for 15 h. The reaction mixture was cooled to ambient temperature and concentrated in vacuo. The residue was triturated with dichloromethane, the solids filtered off, and the filtrate concentrated in vacuo to give the crude product. This crude material was chromatographed over silica gel (10 g), eluting with 1%, 3%, and then 5% methanol/chloroform, to afford, after concentration of appropriate fractions, 0.097 g (53%) of the title compound as an off-white solid with mp 162°–164° C.

EXAMPLE 38

(S)-N-[[3-[3-fluoro-4-[4-(3-hydroxypropyl)-1-piperazinyl]phenyl]-2-oxo-5-oxazolidinyl]methyl]-acetamide A mixture of (S)-N-[[3-[3-fluoro-4-(1-piperazinyl)phenyl]-2-oxo-5-oxazolidinyl]methyl]acetamide (0.200 g, 0.595 mmol), 3-chloro-1-propanol (299 μL, 3.57 mmol) and potassium carbonate (0.493 g, 3.57 mmol) in acetonitrile (12 mL) was heated to reflux for 7 h. The reaction mixture was cooled to ambient temperature and concentrated in vacuo. The crude material was dissolved in 10% methanol/chloroform and absorbed onto silica gel (2 g). Chromatography of this material over silica gel (10 g), eluting with 1%, 3%, and then 6% methanol/chloroform, afforded, after concentration of appropriate fractions, 0.096 g (41%) of the title compound as a white solid with mp 154°–155.5° C.

EXAMPLE 39

(S)-N-[[3-[3,5-difluoro-4-[4-(2-hydroxyethyl)-1-piperazinyl]phenyl]-2-oxo-5-oxazolidinyl]methyl]-acetamide A solution of ( S)-N-[[3-[3,5-difluoro-4-[4-(tert-butoxycarbonyl)- 1-piperazinyl]phenyl]-2-oxo-5-oxazolidinyl]methyl]acetamide (0.400 g, 0.881 mmol) in dichloromethane (3 mL) was treated with trifluoroacetic acid (7 mL) at room temperature for 1 h. The reaction mixture was concentrated in vacuo and the resultant amber syrup combined with 2-chloroethanol (354 μL, 5.27 mmol), potassium carbonate (0.730 g, 5.27 mmol), and acetonitrile (20 mL) and the mixture heated to reflux for 24 h. The reaction mixture was cooled to ambient temperature and concentrated in vacuo. The crude product was chromatographed over silica gel (10 g), eluting with 1%, 3%, and then 6% methanol/chloroform, to afford, after concentration of appropriate fractions, 0.067 g (19%) of the title compound as an off-white solid with mp 172°–174° C.

EXAMPLE 40

(S)-N-[[3-[3-fluoro-4-[4-[3-(4-morpholinyl)-1-oxopropyl]-1-piperazinyl]phenyl]-2-oxo-5-oxazolidinyl]methyl]acetamide 3-(4-Morpholinyl)propionic acid (0.600 g, 2.11 mmol), prepared by condensation of morpholine with ethyl acrylate (3 equivalents) in refluxing ethanol, followed by distillation, saponification (1N aqueous sodium hydroxide, tetrahydrofuran, reflux), neutralization (1N HCl) and lyophilization, was combined with 1,3-dicyclohexylcarbodiimide (0.434 g, 2.11 mmol), 4-(dimethylamino)pyridine (13 mg, 0.11 mmol), (S)-N-[[3-[3-fluoro-4-(1-piperazinyl)phenyl]-2-oxo-5-oxazolidinyl]methyl]acetamide (0.354 g, 1.05 mmol), and 1:1 tetrahydrofuran/dichloromethane (50 mL) at room temperature. After 3 days the reaction mixture was filtered to remove the precipitated 1,3-dicyclohexylurea and the filtrate concentrated in vacuo. The crude product was chromatographed over silica gel (20 g), eluting with a gradient of 1–6% methanol/chloroform, to give 0.446 g (95%) of the title compound as a white solid with mp 209°–210° C.

SCHEME 1

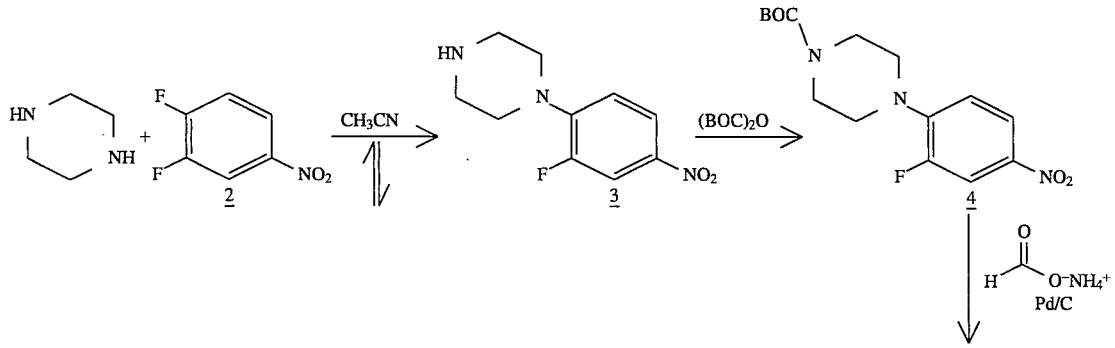

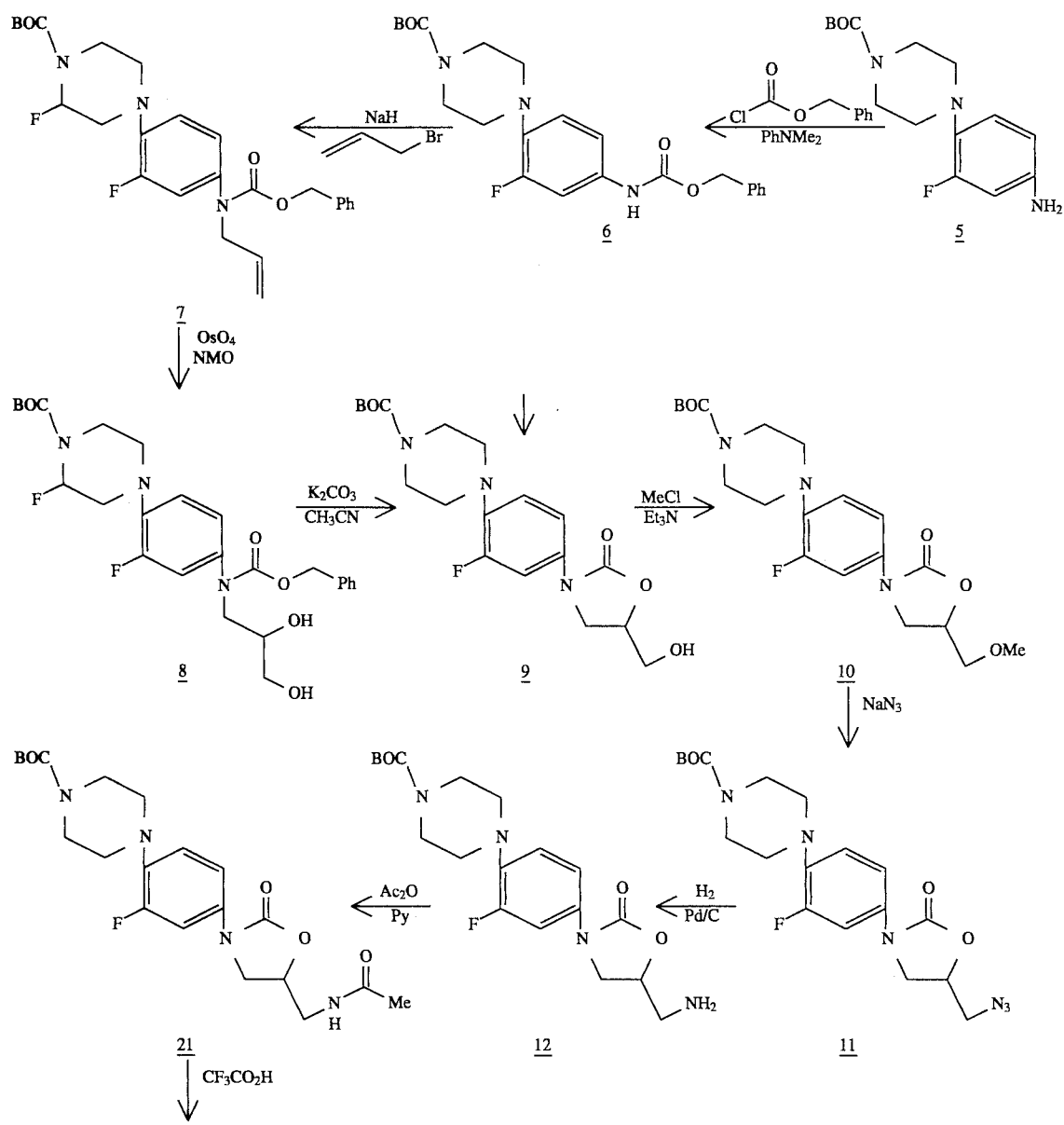
-continued
SCHEME 1

5,547,950
-continued
SCHEME 1
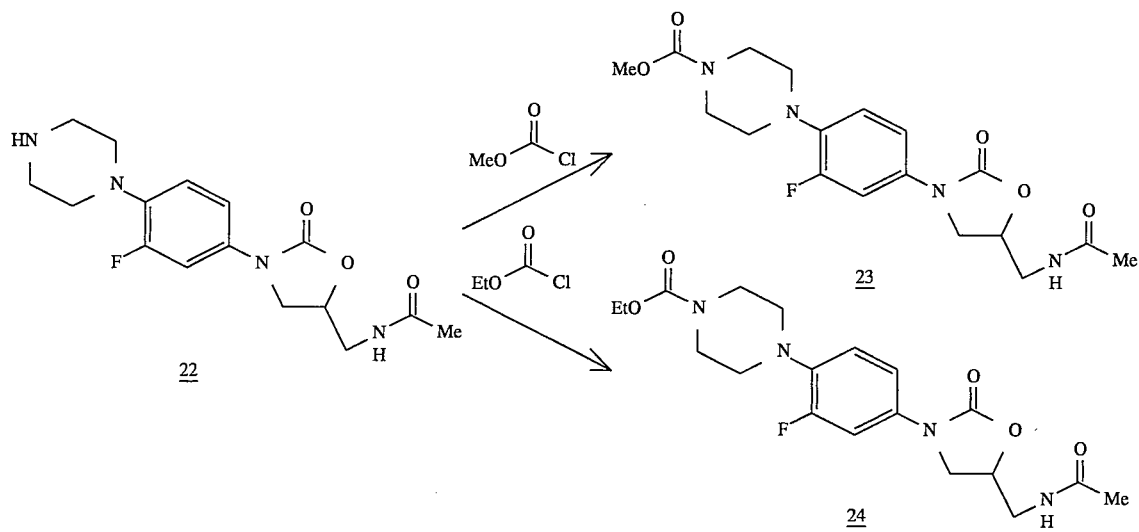
SCHEME 2
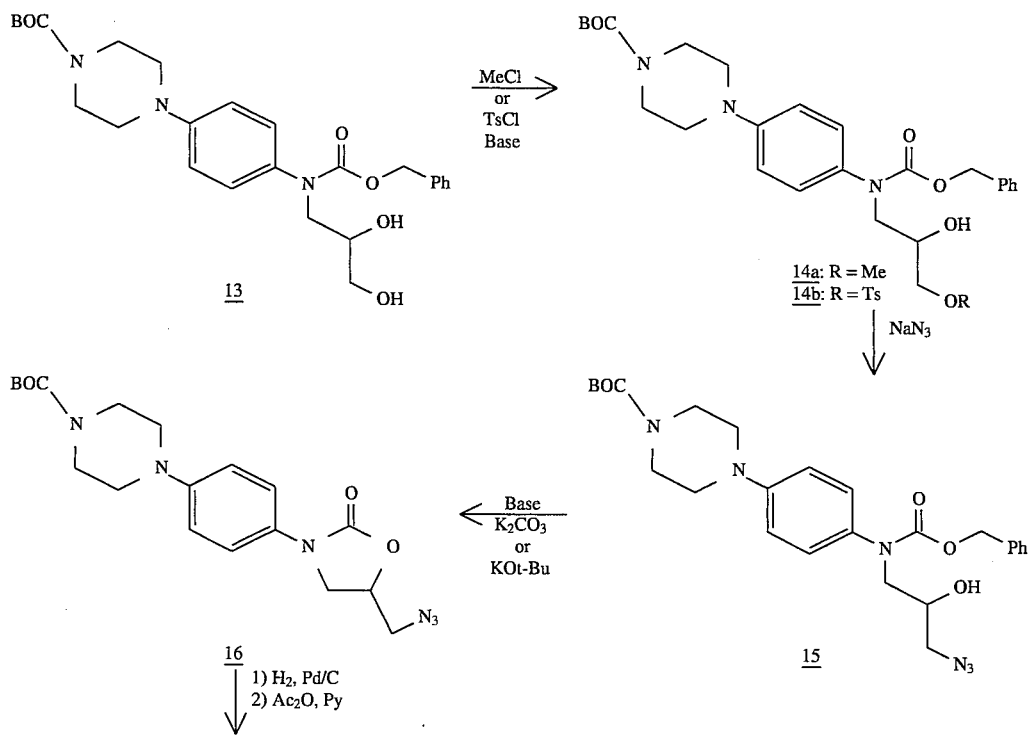

SCHEME 2 (continued)

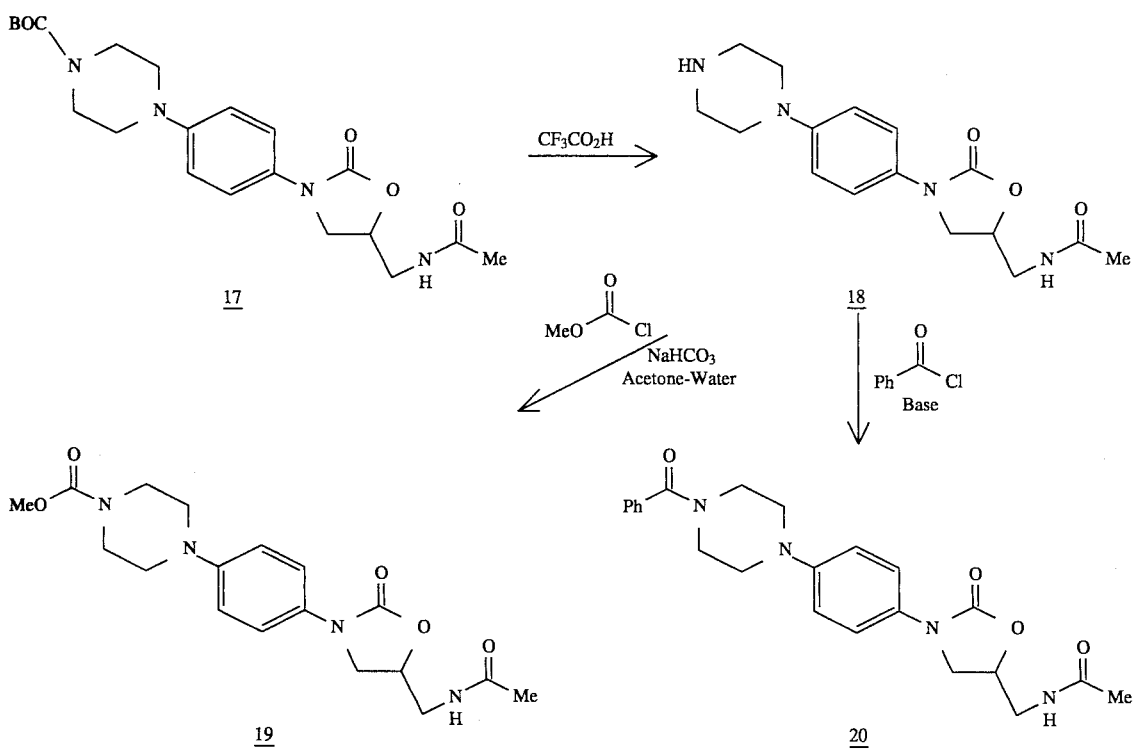

What is claimed:

1. A compound of structural Formula I:

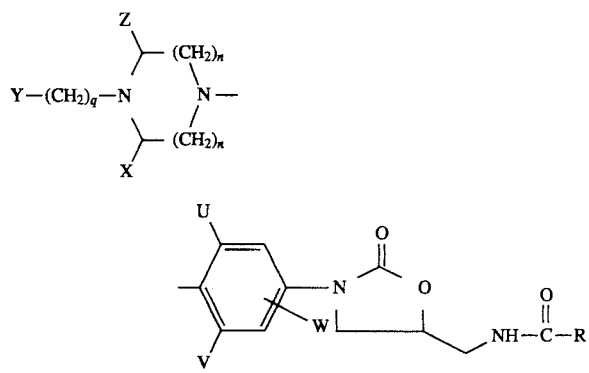

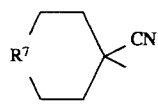

or pharmaceutically acceptable salts thereof wherein:

each n is 1;

Y is a) —C(O)—$C_{1-6}$ alkyl, —C(O)—O—$C_{1-6}$ alkyl or benzoyl, b) —N($R^3$)$_2$ where $R^3$ is independently hydrogen, $C_{1-4}$ alkyl or phenyl which can be substituted with one to three F, Cl, OCH$_3$, OH, NH$_2$, or $C_{1-4}$ alkyl, or c)

(where $R^7$ is O, S, S(O), SO$_2$ or CH$_2$); wherein each occurrence of said $C_{1-6}$ alkyl may be substituted with one or more F, Cl, Br, I, OR$^1$, CO$_2$R$^1$, CN, SR$^1$, or R$^1$ (where R$^1$ is a hydrogen or $C_{1-4}$ alkyl);

X and Z are independently $C_{1-6}$ alkyl, $C_{3-12}$ cycloalkyl or hydrogen;

U, V and W are independently $C_{1-6}$ alkyl, F, Cl, Br, hydrogen or a $C_{1-6}$ alkyl substituted with one or more of F, Cl, Br or I;

R is hydrogen, $C_{1-12}$ alkyl, $C_{3-12}$ cycloalkyl, $C_{1-6}$ alkoxy, $C_{1-6}$ alkyl substituted with one or more F, Cl, Br, I or OH; and q is 0 to 4 inclusive.

2. The compound of claim 1 wherein X and Z are hydrogen.

3. The compound of claim 1 wherein U and V are F and W is hydrogen.

4. The compound of claim 1 wherein U is F and V and W are hydrogen.

5. The compound of claim 1 wherein Y is acetyl, difluoroacetyl, hydroxyacetyl, benzoyl, methoxy carbonyl, ethoxy carbonyl, 2-chloroethoxy carbonyl, 2-hydroxyethoxy carbonyl, 2-methoxyethoxy carbonyl, 2,2,2-trifluoroethoxy carbonyl, carbomethoxymethyl, 2-carbomethoxyethyl, 2-fluoroethoxy carbonyl, or tertiary-butoxy carbonyl.

6. The compound of claim 4 wherein Y is methoxy carbonyl.

7. The compound of claim 1 wherein R is methyl, H, methoxy, or CHCl$_2$.

8. The compound of claim 1 which is an optically pure enantiomer having the S-configuration at C5 of the oxazolidinone ring.

9. The compound of claim 1 which is:

(a) 4-(4-(5-((acetylamino)methyl)-2-oxo-3-oxazolidinyl)-2-fluorophenyl)-1-piperazinecarboxylic acid, methyl ester;

(b) 4-(4-(5-((acetylamino)methyl)-2-oxo-3-oxazolidinyl)- 2-fluorophenyl)-1-piperazinecarboxylic acid, ethyl ester;

(c) 4-(4-(5-((acetylamino)methyl)-2-oxo- 3-oxazolidinyl)phenyl)-1-piperazinecarboxylic acid, methyl ester;

(d) N-((3-(4-(3-Fluoro-4-(4-( 2-hydroxyethyl)carbonyl-1-piperazinyl))phenyl)-2-oxo- 5-oxazolidinyl)methyl)-acetamide; or (e) 4-[4-[5-[(acetylamino)methyl]-2-oxo- 3-oxazolidinyl]-2-fluorophenyl]-1-piperazinecarboxylic acid, 2-methoxyethyl ester.

10. A method for treating microbial infections in warm blooded animals comprising:

administering to a warm blooded animal in need thereof an effective amount of a compound of Formula I

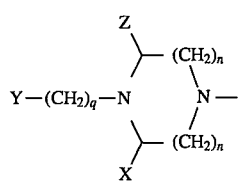

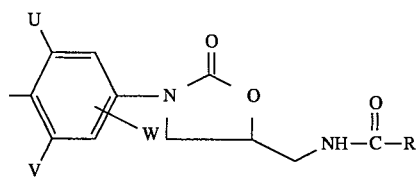

or pharmaceutically acceptable salts thereof wherein:

each n is 1;

Y is a) —C(O)—$C_{1-6}$ alkyl, —C(O)—O—$C_{1-6}$ alkyl or benzoyl, b) —$N(R^3)_2$ and where $R^3$ is independently hydrogen, $C_{1-4}$ alkyl or phenyl which can be substituted with one to three F, Cl, $OCH_3$, OH, $NH_2$, or $C_{1-4}$ alkyl, or

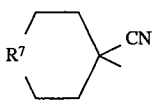 c)

(where $R^7$ is O, S, S(O), $SO_2$ or $CH_2$, wherein each occurrence of said $C_{1-6}$ alkyl may be substituted with one or more F, Cl, Br, I, $OR^1$, $CO_2R^1$, CN, $SR^1$, or $R^1$ (where $R^1$ is a hydrogen or $C_{1-4}$ alkyl);

X and Z are independently $C_{1-6}$ alkyl, $C_{3-12}$ cycloalkyl or hydrogen:

U, V and W are independently $C_{1-6}$ alkyl, F, Cl, Br, hydrogen or a $C_{1-6}$ alkyl substituted with one or more of F, Cl, Br or I;

R is hydrogen, $C_{1-12}$ alkyl, $C_{3-12}$ cycloalkyl, $C_{1-6}$ alkoxy, $C_{1-6}$ alkyl substituted with one or more F, Cl, Br, I or OH; and q is 0 to 4 inclusive.

11. The method of claim 10 wherein said compound is administered in an amount of from about 0.1 to about 100 mg/kg of body weight/day.

12. The method of claim 11 wherein said compound is administered in an amount of from about 3.0 to about 50 mg/kg of body weight/day.

\* \* \* \* \*